(12) United States Patent
Case et al.

(10) Patent No.: US 7,582,110 B2
(45) Date of Patent: Sep. 1, 2009

(54) IMPLANTABLE FRAME WITH VARIABLE COMPLIANCE

(75) Inventors: Brian C. Case, Bloomington, IN (US); Jacob A. Flagle, Bloomington, IN (US); Charles W. Agnew, West Lafayette, IN (US)

(73) Assignee: Cook Incorporated, Bloomington, IN (US)

( * ) Notice: Subject to any disclaimer, the term of this patent is extended or adjusted under 35 U.S.C. 154(b) by 326 days.

(21) Appl. No.: 11/103,137

(22) Filed: Apr. 11, 2005

(65) Prior Publication Data

US 2005/0228486 A1     Oct. 13, 2005

Related U.S. Application Data

(60) Provisional application No. 60/561,739, filed on Apr. 13, 2004.

(51) Int. Cl.
*A61F 2/06* (2006.01)
(52) U.S. Cl. ........................................ 623/1.24
(58) Field of Classification Search ............... 623/1.24, 623/1.26, 1.38
See application file for complete search history.

(56) References Cited

U.S. PATENT DOCUMENTS

| | | | |
|---|---|---|---|
| 3,063,967 A | 11/1962 | Schultz | |
| 3,063,968 A | 11/1962 | Schultz | |
| 3,169,945 A | 2/1965 | Hostettler et al. | |
| 3,391,126 A | 7/1968 | Baggett et al. | |
| 3,645,941 A | 2/1972 | Snapp et al. | |
| 3,912,692 A | 10/1975 | Casey et al. | |
| 3,942,532 A | 3/1976 | Hunter et al. | |
| 4,052,988 A | 10/1977 | Doddi et al. | |
| 4,076,807 A | 2/1978 | Trinh et al. | |
| 4,243,775 A | 1/1981 | Rosensaft et al. | |
| 4,300,565 A | 11/1981 | Rosensaft et al. | |
| 4,429,080 A | 1/1984 | Casey et al. | |
| 4,440,789 A | 4/1984 | Mattei et al. | |
| 4,549,921 A | 10/1985 | Wolfe, Jr. | |
| 4,559,945 A | 12/1985 | Koelmel et al. | |
| 4,591,630 A | 5/1986 | Gertzman et al. | |
| 4,605,730 A | 8/1986 | Shalaby et al. | |
| 4,624,256 A | 11/1986 | Messier et al. | |
| 4,643,191 A | 2/1987 | Bezwada et al. | |
| 4,643,734 A | 2/1987 | Lin | |
| 4,653,497 A | 3/1987 | Bezwada et al. | |

(Continued)

FOREIGN PATENT DOCUMENTS

EP      460428      12/1991

(Continued)

OTHER PUBLICATIONS

D.K. Gilding, A.M. Reed, "Biodegradable polymers for use in surgery—polyglycolic/poly(actic acid) homo- and copolymers: 1," *Polymer*, 1979, vol. 20, 1459-1464.

(Continued)

*Primary Examiner*—William H. Matthews
(74) *Attorney, Agent, or Firm*—Brinks Hofer Gilson & Lione

(57) ABSTRACT

Medical devices for implantation in a body vessel, and methods of using and making the same, are provided. Embodiments of the invention relate to medical devices comprising a frame having a compliance that can change upon implantation of the medical device within the lumen of a body vessel. Controlled fracture or bioabsorption of frame material can, in some embodiments, increase the compliance of a frame after implantation. Medical devices comprising a frame and one or more valve members adapted to regulate fluid flow in a body vessel, such as a vein, are also provided.

20 Claims, 7 Drawing Sheets

U.S. PATENT DOCUMENTS

| | | | |
|---|---|---|---|
| 4,700,704 A | 10/1987 | Jamiolkowski et al. | |
| 4,776,337 A | 10/1988 | Palmaz | |
| 4,788,979 A | 12/1988 | Jarrett et al. | |
| 4,791,929 A | 12/1988 | Jarrett et al. | |
| 4,816,028 A | 3/1989 | Kapadia et al. | |
| 4,838,267 A | 6/1989 | Jamiolkowski et al. | |
| 4,856,516 A | 8/1989 | Hillstead | |
| 4,893,623 A | 1/1990 | Rosenbluth | |
| 4,969,458 A | 11/1990 | Wiktor | |
| 4,994,071 A | 2/1991 | MacGregor | |
| 4,994,074 A | 2/1991 | Bezwada et al. | |
| 5,007,923 A | 4/1991 | Bezwada et al. | |
| 5,019,085 A | 5/1991 | Hillstead | |
| 5,047,048 A | 9/1991 | Bezwada et al. | |
| 5,076,807 A | 12/1991 | Bezwada et al. | |
| 5,080,665 A | 1/1992 | Jarrett et al. | |
| 5,085,629 A | 2/1992 | Goldberg et al. | |
| 5,100,433 A | 3/1992 | Bezwada et al. | |
| 5,104,404 A | 4/1992 | Wolff | |
| 5,116,365 A | 5/1992 | Hillstead | |
| 5,133,755 A | 7/1992 | Brekke | |
| 5,135,536 A | 8/1992 | Hillstead | |
| 5,178,618 A | 1/1993 | Kandarpa | |
| 5,234,457 A | 8/1993 | Andersen | |
| 5,282,824 A | 2/1994 | Gianturco | |
| 5,293,879 A | 3/1994 | Vonk et al. | |
| 5,314,472 A | 5/1994 | Fontaine | |
| 5,342,387 A | 8/1994 | Summers | |
| 5,366,473 A | 11/1994 | Winston et al. | |
| 5,383,892 A | 1/1995 | Cardon et al. | |
| 5,389,106 A | 2/1995 | Tower | |
| 5,393,594 A | 2/1995 | Koyfman et al. | |
| 5,412,068 A | 5/1995 | Tang et al. | |
| 5,421,955 A | 6/1995 | Lau et al. | |
| 5,443,496 A | 8/1995 | Schwartz | |
| 5,449,373 A | 9/1995 | Pinchasik | |
| 5,468,253 A | 11/1995 | Bezwada et al. | |
| 5,507,767 A | 4/1996 | Maeda et al. | |
| 5,514,154 A | 5/1996 | Lau et al. | |
| 5,522,841 A | 6/1996 | Roby et al. | |
| 5,527,354 A | 6/1996 | Fontaine et al. | |
| 5,540,712 A | 7/1996 | Kleshinski et al. | |
| 5,540,713 A | 7/1996 | Schnepp-Pesch et al. | |
| 5,549,662 A | 8/1996 | Fordenbacher | |
| 5,549,663 A | 8/1996 | Cottone, Jr. | |
| 5,554,181 A | 9/1996 | Das | |
| 5,591,197 A | 1/1997 | Orth et al. | |
| 5,591,198 A | 1/1997 | Boyle et al. | |
| 5,607,442 A | 3/1997 | Fischell et al. | |
| 5,607,445 A | 3/1997 | Summers | |
| 5,613,981 A | 3/1997 | Boyle et al. | |
| 5,630,829 A | 5/1997 | Lauterjung | |
| 5,636,641 A | 6/1997 | Fariabi | |
| 5,643,312 A | 7/1997 | Fischell et al. | |
| 5,653,727 A | 8/1997 | Wiktor | |
| 5,681,346 A | 10/1997 | Orth et al. | |
| 5,697,971 A | 12/1997 | Fischell et al. | |
| 5,705,181 A | 1/1998 | Cooper et al. | |
| 5,713,920 A | 2/1998 | Bezwada et al. | |
| 5,725,572 A | 3/1998 | Lam et al. | |
| 5,728,158 A | 3/1998 | Lau et al. | |
| 5,733,303 A | 3/1998 | Israel et al. | |
| 5,735,893 A | 4/1998 | Lau et al. | |
| 5,741,327 A | 4/1998 | Frantzen | |
| 5,749,919 A | 5/1998 | Blanc | |
| 5,755,776 A | 5/1998 | Al-Saadon | |
| 5,759,192 A | 6/1998 | Saunders | |
| 5,766,238 A | 6/1998 | Lau et al. | |
| 5,776,161 A | 7/1998 | Globerman | |
| 5,807,404 A | 9/1998 | Richter | |
| 5,855,600 A | 1/1999 | Alt | |
| 5,895,420 A | 4/1999 | Mirsch, II et al. | |
| 6,090,127 A | 7/2000 | Globerman | |
| 6,287,332 B1 | 9/2001 | Bolz et al. | |
| 6,287,336 B1 | 9/2001 | Globerman et al. | |
| 6,428,570 B1 | 8/2002 | Globerman | |
| 6,656,216 B1 | 12/2003 | Hossainy et al. | |
| 7,273,492 B2 | 9/2007 | Cheng et al. | 632/1.11 |
| 2001/0039450 A1* | 11/2001 | Pavcnik et al. | 623/1.24 |
| 2001/0041930 A1 | 11/2001 | Globerman et al. | |
| 2003/0153972 A1* | 8/2003 | Helmus | 623/1.15 |
| 2004/0167619 A1 | 8/2004 | Case et al. | |
| 2007/0185560 A1 | 8/2007 | Roeder et al. | 623/1.15 |

FOREIGN PATENT DOCUMENTS

| | | |
|---|---|---|
| EP | 0 493 788 A1 | 7/1992 |
| EP | 0800801 A1 | 10/1997 |
| WO | WO 9721399 | 6/1997 |
| WO | WO 9725937 | 7/1997 |
| WO | WO 9732543 | 9/1997 |
| WO | WO 9818404 | 5/1998 |
| WO | WO 03/063733 A1 | 8/2003 |
| WO | WO 03/088872 A1 | 10/2003 |

OTHER PUBLICATIONS

D.K. Gilding, "Biodegradable Polymers," *Biocompatibility of Clinical Implant Materials*, Chap. 9, pp. 209-232, 1981.

Gabriel Helmlinger, Bradford C. Berk, Robert M. Nerem, "Calcium responses of endothelial cell monolayers subjected to pulsatile and steady laminar flow differ," *Am. J. Physiol. Cell Physiol.*, 269: C367-C375, 1995.

Matthias Chiquet, Mark Matthisson, Manuel Koch, Michael Tannheimer, Ruth Chiquet-Ehrismann, "Regulation of extracellular matrix synthesis by mechanical stress," *Biochem. Cell Biol.* 74, 737-744 (1996).

Yi-Shuan Li, John Y.-J. Shyy, Song Li, Jongdae Lee, Bing Us, Michael Karin, Shu Chien, "The Ras-JNK Pathway Is Involved in Shear-Induced Gene Expression," *Molecular and Cellular Biologyl*, 1996, 5947-5954.

Dana E. Perrin, James P. English, "Polycaprolactone," *Handbook of Bioabsorbable Polymers*, 1997 63-76.

Wai Hung Wong, David J. Mooney, "Synthesis and Properties of Biodegradable Polymers Used as Synthetic Matrices for Tissue Engineering," I Synthetic Biodegradable Polymer Scaffoldsl, 1997 51-82.

Shu Chien, Song Li, John Y-J Shyy, "Effects of Mechanical Forces on Signal Transdution and Gene Expression in Endothelial Cells," *Hypertension* 31, 162-169 1998.

Lamba, et al., "Degradation of Polyurethanes," *Polyurethanes in Biomedical Applications*, 181-204 1998.

Matthias Chiquet, "Regulation of extracellular matrix gene expression by mechanical stress," *Matrix Biol.*, 417-426, 1999.

Marcy Wong, Mark Siegrist, Xuesong Cao, "Cyclic compression of articular cartilage explants is associated with progressive consolidation and altered expression pattern of extracellular matrix proteins," *Matrix Biology*, 391-399, 1999.

Alan J. Grodzinsky, Marc E. Levenston, Moonsoo Jin, Eliot H. Frank, "Cartilage Tissue Remodeling in Response to Mechanical Forces," *Annual Review of Biomedical Engineering*, 691-713, 2000.

V.C. Mudera, R. Pleass, M. Eastwood, R. Tarnuzzer, G. Schultz, P. Khaw, D.A. McGrouther, R.A. Brown, "Molecular Responses of Human Dermal Fibroblasts to Dual Cues: Contact Guidance and Mechanical Load," *Cell Motility and the Cytoskeleton*, 45: 1-9, 2000.

Christof Schild, Beat Trueb, "Mechanical Stress is Required for High-Level Expression of Connective Tissue Growth Factor," *Experimental Cell Research*, 274: 83-91, 2002.

Communication Relating to the Results of the Partial International Search—Annex to Form PCT/ISA/206 Invitation to Pay Additional Fees for corresponding International Application No. PCT/US2005/012421.

* cited by examiner

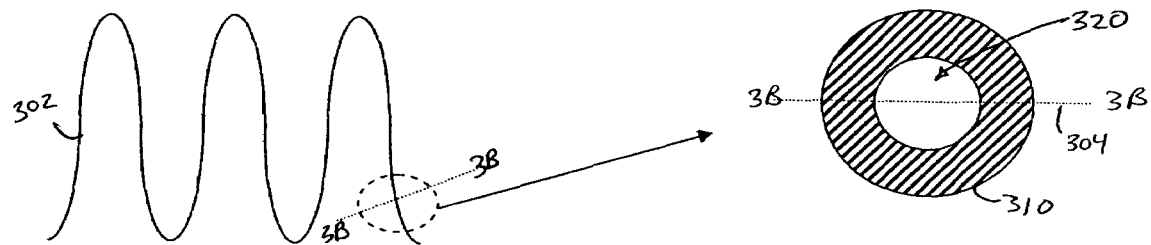
Figure 3A
Figure 3B
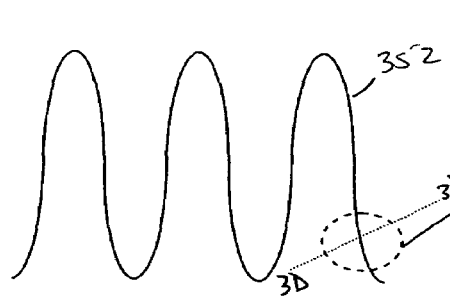
Figure 3C
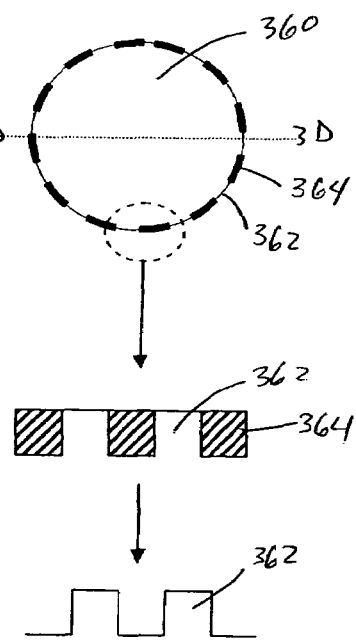
Figure 3D
Figure 3E

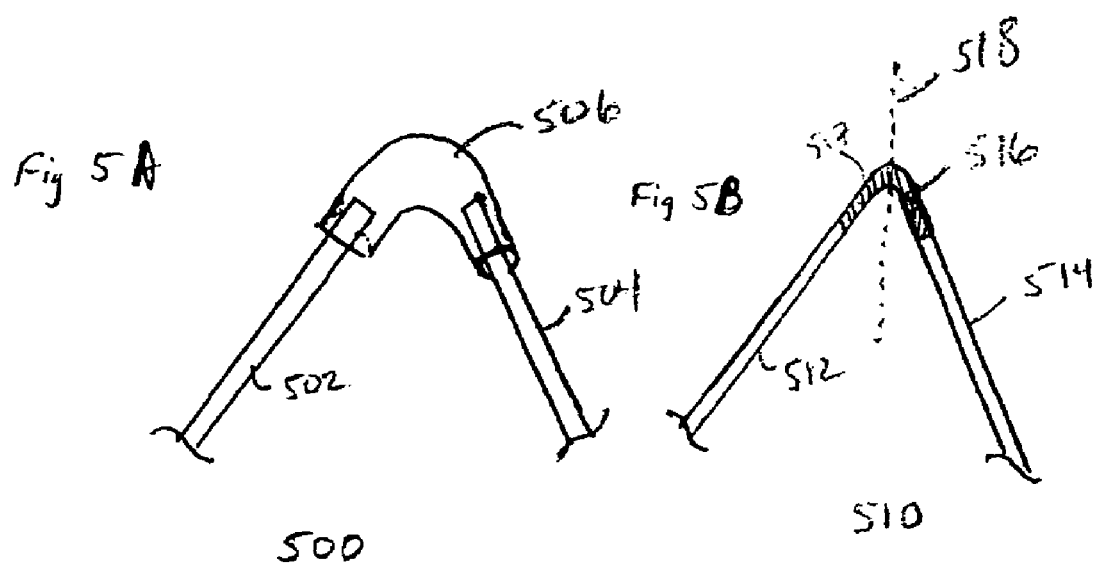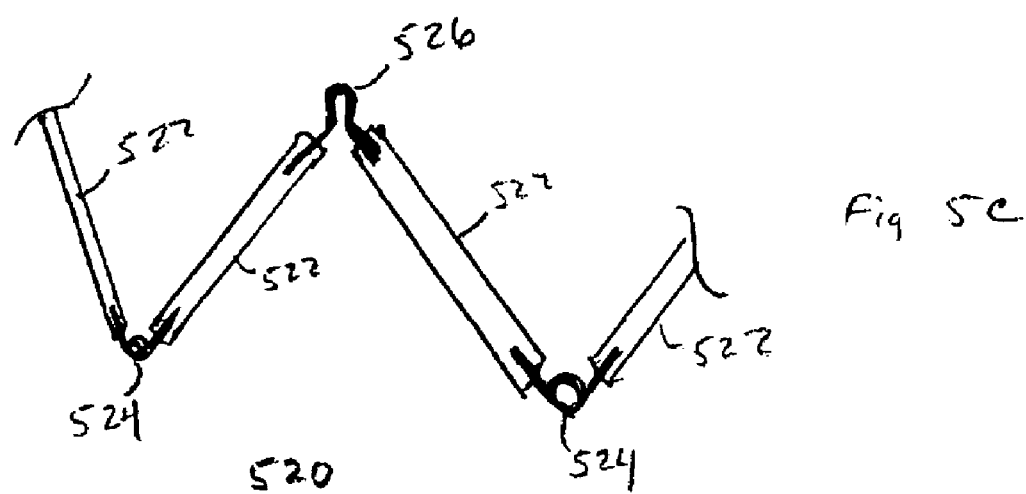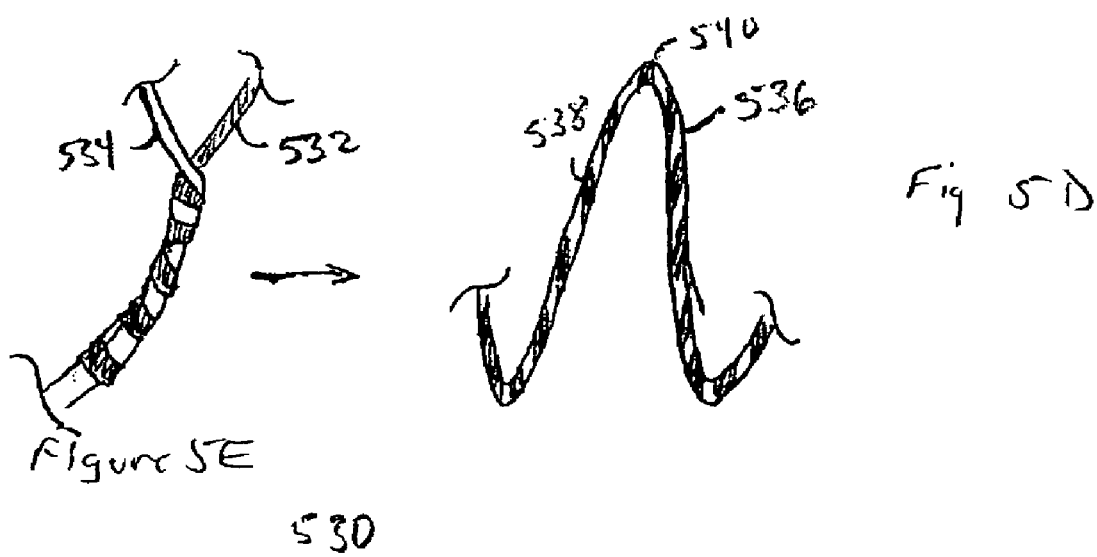

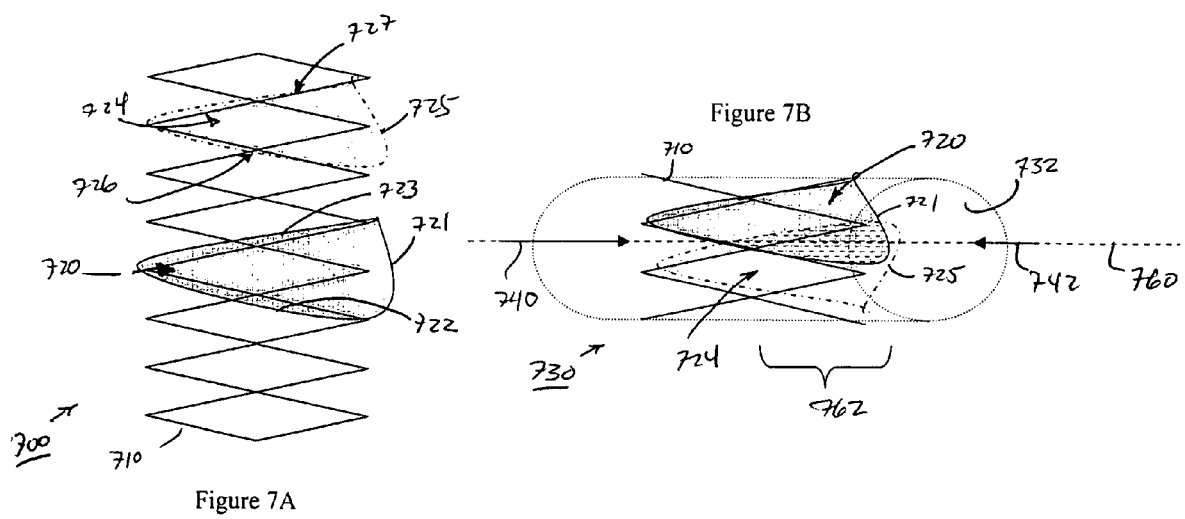
Figure 7A
Figure 7B
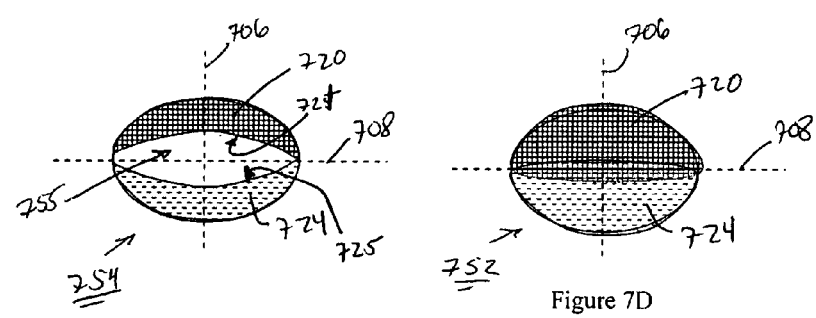
Figure 7C
Figure 7D

IMPLANTABLE FRAME WITH VARIABLE COMPLIANCE

RELATED APPLICATION

This application claims priority to U.S. Provisional Patent Application No. 60/561,739, entitled "Implantable Frame With Variable Compliance Material," filed Apr. 13, 2004, which is incorporated herein by reference in its entirety.

TECHNICAL FIELD

The present invention relates to medical devices. More particularly, the invention relates to medical devices for implantation in a body vessel.

BACKGROUND

Various implantable medical devices are advantageously inserted within various body vessels, for example from an implantation catheter. Minimally invasive techniques and instruments for placement of intraluminal medical devices have been developed to treat and repair such undesirable conditions within body vessels, including treatment of venous valve insufficiency. Intraluminal medical devices can be deployed in a vessel at a point of treatment, the delivery device withdrawn from the vessel, and the medical device retained within the vessel to provide sustained improvement in vascular valve function. For example, implantable medical devices can function as a replacement venous valve, or restore native venous valve function by bringing incompetent valve leaflets into closer proximity. Such devices can comprise an expandable frame configured for implantation in the lumen of a body vessel, such as a vein. Venous valve devices can further comprise features that provide a valve function, such as opposable leaflets.

Implantable medical devices can comprise frames that are highly compliant, and therefore able to conform to both the shape of the lumen of a body vessel as well as respond to changes in the body vessel shape. Dynamic fluctuations in the shape of the lumen of a body vessel pose challenges to the design of implantable devices that conform to the interior shape of the body vessel. For instance, the flow velocity and diameter of veins do not remain essentially constant at a given systemic vascular resistance. Instead, the shape of vein lumens can fluctuate dynamically in response to the respiration, body position, central venous pressure, arterial inflow and calf muscle pump action of a mammalian subject. The veins also provide the principal volume capacitance organ. For example, an increase of almost 100% in the diameter of the common femoral vein has been observed in human patients simply by rotation of the patient by about 40 degrees, corresponding to a four-fold increase in blood flow volume. Moneta et al., "Duplex ultrasound assessment of venous diameters, peak velocities and flow patterns," J. Vasc. Surg. 8; 286-291 (1988). The shape of a lumen of a vein can undergo dramatic dynamic change as a result of varying blood flow velocities and volumes therethrough, presenting challenges for designing implantable intraluminal prosthetic devices that are compliant to the changing shape of the vein lumen.

However, an implantable medical device comprising a highly compliant frame can present other drawbacks in some applications, such as for providing a support structure for remodelable material. For treatment of many conditions, it is desirable that implantable medical devices comprise remodelable material. Implanted remodelable material provides a matrix or support for the growth of new tissue thereon, and remodelable material is resorbed into the body in which the device is implanted. Common events during this remodeling process include: widespread neovascularization, proliferation of granulation mesenchymal cells, biodegradation/resorption of implanted remodelable material, and absence of immune rejection. By this process, autologous cells from the body can replace the remodelable portions of the medical device.

Mechanical loading of remodelable material during the remodeling process has been shown to advantageously influence the remodeling process. For example, the remodeling process of one type of remodelable material, extracellular matrix (ECM), is more effective when the material is subject to certain types and ranges of mechanical loading during the remodeling process. See, e.g., M. Chiquet, "Regulation of extracellular matrix gene expression by pressure," Matrix Biol. 18(5), 417-426 (October 1999). Mechanical forces on a remodelable material during the remodeling process can affect processes such as signal transduction, gene expression and contact guidance of cells. See, e.g., V C Mudera et al., "Molecular responses of human dermal fibroblasts to dual cues: contact guidance and mechanical load," Cell Motil. Cytoskeleton, 45(1):1-9 (June 2000).

A variety of remodelable materials are available for use in implantable medical devices. For instance, naturally derived or synthetic collagenous materials can be used to provide remodelable surfaces on implantable medical devices. Naturally derived or synthetic collagenous material, such as extracellular matrix material, are another category of remodelable materials that include, for instance, submucosa, renal capsule membrane, dura mater, pericardium, serosa, and peritoneum or basement membrane materials. One specific example of an extracellular matrix material is small intestine submucosa (SIS). When implanted, SIS can undergo remodeling and induces the growth of endogenous tissues upon implantation into a host. SIS has been used successfully in vascular grafts, urinary bladder and hernia repair, replacement and repair of tendons and ligaments, and dermal grafts.

Presently, medical devices often comprise frames with a fixed degree of compliance that does not change over time. Therefore, optimizing the degree to which a medical device for implantation within a body vessel is compliant to changes in the shape of the body vessel can present a trade-off between competing factors. For example, a medical device comprising a highly compliant frame can minimize distortion of a body vessel by being highly responsive to changes in the shape of the body vessel. However, a frame with less compliance may provide inadequate mechanical loading to material attached to the frame to allow or promote certain desirable processes to occur within the attached material, such as remodeling, or within the body vessel. In this example, frame compliance is a trade-off between enabling the remodeling of material attached to the frame, and minimizing the distortion or disruption of the body vessel.

What is needed are medical devices that provide changing compliance over time. There exists a need in the art for an implantable prosthetic device frame that is capable of balancing concerns of conforming to the shape of a body vessel lumen and providing optimal tension on a remodelable material attached to the frame.

By providing frames with compliance that can vary with time, embodiments of the present invention enable one skilled in the art to design, make and use medical devices that provide desired levels of compliance at different time periods. Medical devices with variable compliance can provide, for example, an optimal amount of tension on an attached remodelable material during the remodeling process, and then provide increased compliance and minimal body vessel distortion after the remodeling process is completed.

SUMMARY

The invention relates to medical devices for implantation in a body vessel. More specifically, preferred embodiments of the invention relate to a medical device comprising a frame having a first compliance in a first direction, and at least a portion of the frame responsive to conditions within a body vessel to increase the compliance of the frame along at least the first direction. In one aspect, the frame comprises a portion that fractures in a controlled manner to increase the compliance of the frame. In a second aspect, the frame comprises a bioabsorbable material, the bioabsorption of which increases the compliance of the frame.

In a first embodiment, a medical device can comprise an implantable frame. In one aspect, the implantable frame can comprise a portion that fractures in a controlled manner upon implantation, thereby increasing the compliance of the frame. Preferably, the medical device is designed to protect the body vessel from damage during or after the fracture of a portion of the frame. The frame may, in some embodiments, continue to provide an increased and sustained level of compliance within a vessel after the fracture of a portion of the frame. A frame having a first compliance in a first direction can, upon fracture of a portion of the frame, have a second compliance after the fracture of the portion of the frame. The fracturing of the portion of the frame can result in a sudden change in the compliance of the frame in one aspect, or a more gradual change in compliance in other aspects. In another aspect, a medical device can comprise one or more bioabsorbable materials, and absorption of a bioabsorbable material can increase the compliance of the frame in a first direction. Absorption of the bioabsorbable material can gradually change the compliance of the frame, for example by reducing the cross section or surface area of a portion of the frame. In another aspect, absorption of the bioabsorbable material can allow for the controlled fracture of a portion of the frame, resulting in a sudden change in the compliance of the frame.

The implantable frame can have any suitable structure. The implantable frame preferably comprises a plurality of struts, which can be of any suitable structure or orientation to allow the frame to provide a first compliance in a first direction, and at least a portion of the frame responsive to conditions within a body vessel to increase the compliance of the frame along the first direction. Preferably, the frame comprises a plurality of struts connected by alternating bends. For example, the frame can be a sinusoidal annular ring member comprising a series of struts in a "zig-zag" pattern. The frame can also comprise multiple annular ring members with struts in a "zig-zag" pattern, for example, by connecting the annular ring members end to end, or in an overlapping fashion. In some embodiments, the struts are substantially aligned along the surface of a tubular plane, substantially parallel to the longitudinal axis of the support frame.

The implantable frame can be made from any suitable material. The implantable frame, or any portion of the frame, can optionally be made from a bioabsorbable material. The frame can further comprise a first bioabsorbable material or a non-bioabsorbable material as a "core" material. The core material can be at least partially enclosed by a second bioabsorbable material. The frame can have multiple bioabsorbable materials stacked on all or part of the surface of a core material. The frame can also comprise a surface area presenting both a bioabsorbable material and a non-bioabsorbable material, and absorption of the bioabsorbable material can increase the surface area of the frame (for example, by increasing the surface area of the non-bioabsorbable frame portion), resulting in an increase of the compliance of the frame in a first direction. The frame can further include one or more support arms comprising a bioabsorbable material, and absorption of the bioabsorbable material can increase the compliance of the frame in the first direction. Absorption of bioabsorbable material of a frame can also allow a portion of the frame to fracture in a controlled fashion, for example in response to external force or during the remodeling process.

In a second embodiment, a medical device can comprise an implantable frame and a remodelable material attached to the frame. Preferably, the remodelable material is subject to a mechanical load adequate to allow remodeling of the remodelable material when the frame has the first compliance in the first direction. A change in the compliance of the frame preferably changes the mechanical load on the remodelable material. Any suitable remodelable material may be used. Preferably, the remodelable material is an extracellular matrix material (ECM), such as small intestine submucosa (SIS). Other materials, such as suitable synthetic polymer materials, can be attached to the frame.

In a third embodiment, the medical device can comprise a frame and a means for regulating fluid through a body vessel. In some embodiments, the fluid can flow through the frame, while other embodiments provide for fluid flow through a lumen defined by the frame, or a portion of the frame. Some embodiments comprise a frame and a first valve member connected to the frame for regulating fluid flow within a body vessel. A valve member, according to some embodiments, can comprise a leaflet having a free edge, responsive to the flow of fluid through the body vessel. For example, one or more valve members attached to a frame may, in one embodiment, permit fluid to flow through a body vessel in a first direction while substantially preventing fluid flow in the opposite direction. In some embodiments, the valve member comprises an extracellular matrix material, such as small intestine submucosa (SIS). The valve member can be made from any suitable material, including a remodelable material or a synthetic polymer material.

The medical devices of some embodiments can be expandable from a compressed delivery configuration to an expanded deployment configuration. Preferably, the implantable frame can be expanded from a compressed tubular configuration to an expanded tubular configuration. Preferably, the compressed tubular configuration is adapted for implantation in a body vessel using a catheter-based delivery system. Implantation in the body vessel can be performed by expanding the implantable frame within the body vessel from the compressed configuration to a radially expanded configuration using any suitable means. For example, medical devices can be delivered intraluminally, using various types of delivery catheters, and be expanded by conventional methods such as balloon expansion or self expansion. Also provided are embodiments wherein the frame comprises a means for orienting the frame within a body lumen. For example, the frame can comprise a marker, or a delivery device comprising the frame can provide indicia relating to the orientation of the frame within the body vessel.

Other embodiments provide methods of making the medical devices. Still other embodiments provide methods of treating a subject, which can be animal or human, comprising the step of implanting one or more support frames as described herein. Other methods further comprise the step of implanting one or more frames attached to one or more valve members, as described herein. In some embodiments, methods of treating may also include the step of delivering a medical device to a point of treatment in a body vessel, or deploying a medical device at the point of treatment. Methods for treating certain conditions are also provided, such as venous valve insufficiency, varicose veins, esophageal reflux, restenosis or atherosclerosis.

Methods for delivering a medical device as described herein to any suitable body vessel are also provided, such as a vein, artery, biliary duct, ureteral vessel, body passage or portion of the alimentary canal. In some embodiments, medical devices having a frame with a compressed delivery configuration with a very low-profile, small collapsed diameter and great flexibility, may be able to navigate small or tortuous paths through a variety of body vessels. A low-profile medical device may also be useful in coronary arteries, carotid arteries, vascular aneurysms, and peripheral arteries and veins (low profile, renal, iliac, femoral, popliteal, sublavian, aorta, intercranial, etc.). Other nonvascular applications include gastrointestinal, duodenum, biliary ducts, esophagus, urethra, reproductive tracts, trachea, and respiratory (e.g., bronchial) ducts. These applications may or may not require a sheath covering the medical device.

The invention includes other embodiments within the scope of the claims, and variations of all embodiments, and is limited only by the claims made by the Applicants. Additional understanding of the invention can be obtained by referencing the detailed description of embodiments of the invention, below, and the appended drawings.

BRIEF DESCRIPTION OF THE DRAWINGS

FIG. 3A is a diagram, and FIG. 3B is a corresponding cross section, of a portion of a frame comprising a non-bioabsorbable core material surrounded by a bioabsorbable material. FIG. 3C is a diagram, and FIG. 3D is a corresponding cross section, of a portion of another frame comprising a surface presenting both bioabsorbable and non-bioabsorbable material. Bioabsorption of the bioabsorbable material increases the compliance of both frames.

FIG. 5A, FIG. 5B, FIG. 5C, FIG. 5D and FIG. 5E show portions of various frames that form part of a medical device.

FIG. 6A shows a first medical device in a planar configuration; FIG. 6B shows the first medical device in a tubular configuration. FIG. 6C shows a second medical device in a planar configuration; FIG. 6D shows the second medical device in a tubular configuration.

FIGS. 7A-7D show a medical device comprising a first leaflet and a second leaflet attached to a frame. FIG. 7A shows the medical device in a planar configuration. FIG. 7B shows the medical device in a tubular configuration. FIG. 7C shows an end view of the medical device of FIG. 7B in an open valve configuration; FIG. 7D shows an end view of the medical device of FIG. 7B in a closed valve configuration.

DETAILED DESCRIPTION OF EMBODIMENTS

Figure 1A:
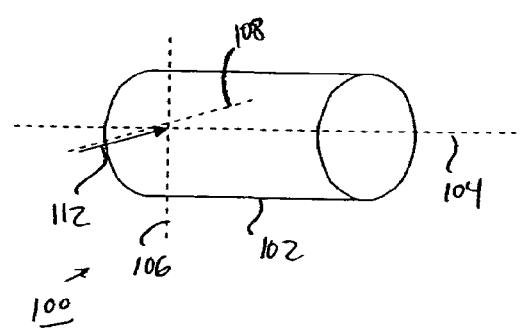
FIG. 1A is a schematic.

The following detailed description and appended drawings describe and illustrate various exemplary embodiments of the invention. The description and drawings serve to enable one skilled in the art to make and use the invention, and are not intended to limit the scope of the invention in any manner.

The invention provides medical devices for implantation in a body vessel, methods of making the medical devices, and methods of treatment that utilize the medical devices.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

The invention relates to medical devices for implantation in a body vessel. More specifically, preferred embodiments of the invention relate to a medical device comprising a frame having a first compliance in a first direction, and at least a portion of the frame responsive to conditions within a body vessel to increase the compliance of the frame along the first direction. The frame can be expandable or non-expandable, and be formed from any suitable materials.

The recitation of a "first" direction is provided as an example. Any suitable orientation or direction may correspond to a "first" direction. The medical devices of the embodiments described herein may be oriented in any suitable absolute orientation with respect to a body vessel. For example, the first direction can be a radial direction in some embodiments.

"Compliance" refers to the displacement of the body frame in response to a given force directed inward toward the center of the frame. Increased compliance is measured by comparing the frame displacement in response to the same force applied inward to the frame along the same direction at two different points in time. Preferably, the medical device comprises a frame having a first compliance in a first direction, and at least a portion of the frame responsive to one or more conditions within a body vessel to increase the compliance of the frame along the first direction. The increase in compliance of the frame upon implantation can occur in several ways. For example, a portion of a frame can be bioabsorbed or fracture in a controlled fraction to increase the frame compliance in a first direction. In some embodiments, the frame can comprise various materials or configurations to provide an increased compliance after a period of time after implantation.

Implantable Frames

In a first embodiment, a medical device comprises an implantable frame. Preferably, the implantable frame includes one or more materials selected to reduce the compliance of the frame in at least one direction after a desired period of time. In one aspect, the frame comprises a material selected to fracture after a desirable amount of sustained pressure within a body vessel. In another aspect, the frame comprises a material selected to be absorbed within a body vessel and absorption of the bioabsorbable material reduces the compliance of the frame after a desired period of time.

In a first aspect, a portion of an implantable frame is designed to fracture after a desired period of time after implantation. An implantable frame having a first compliance in a first direction can, upon fracture of the frame portion, have a second compliance in the first direction after the fracture of the material. Preferably, the second compliance is less than the first compliance. Preferably, the fracture is a controlled fracture, meaning that the fracture does not harm surrounding tissue. In one embodiment, the frame can fracture without presenting exposed ends to surrounding tissue. In another embodiment, the frame can cleanly break, such that the fractured ends of the frame can be shielded from the surrounding material. In another embodiment, the frame can be embedded in remodeled tissue when the fracture occurs, and the frame can be designed to fracture in a manner that will not harm surrounding tissue (for example, by crumbling and then being bioabsorbed). Preferably, the frame is designed to comply with applicable governmental regulatory guidelines promulgated.

In a second aspect, an implantable frame comprises a bioabsorbable material. Preferably, absorption of the bioabsorbable material increase the compliance of the implantable frame in a first direction. The compliance of the frame can occur by various mechanisms during or after absorption of at least a portion of the bioabsorbable material. For example, the compliance of a frame comprising a bioabsorbable material can gradually increase with the bioabsorption of the bioabsorbable material. The bioabsorption of a bioabsorbable support arm can also result in a fracture of a portion of the implantable frame after a desired period of implantation. For example, a delayed fracture may occur after a bioabsorbable material is absorbed after 6 months of implantation in a blood vessel, in response to shear forces of blood flow, thereby suddenly increasing the compliance of the frame. In another embodiment, micro fractures in portions of the frame can increase the flexibility of portions of the frame, thereby increasing the compliance of the frame along a first direction.

Figure 1B:
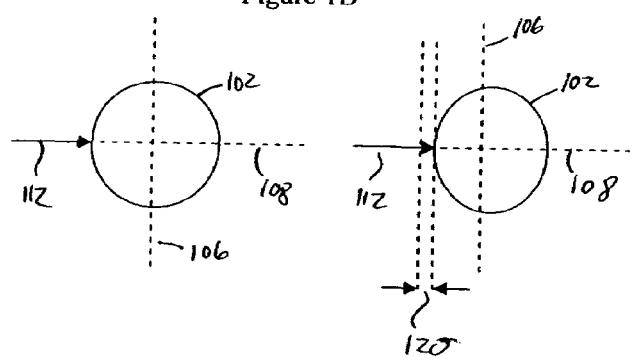
FIG. 1B is a cross-sectional view, of a medical device having a first compliance in a first direction.

FIG. 1A is a perspective and FIG. 1B is an end view of a medical device 100 at a first time having a first compliance 190 in a first direction 108. The medical device 100 has a tubular frame 102 with a longitudinal axis 104, shown with a first direction 108 and a second direction 106. In this embodiment, the direction 108 is perpendicular to the second radial direction 106, and both of these directions are perpendicular to the longitudinal axis 104 of the tubular frame body 102. However, other configurations are also within the scope of the invention. For instance, other embodiments may provide directions that are not perpendicular to each other or to the longitudinal axis of either the frame or the body vessel.

The medical device 100 is shown as deployed in an expanded configuration in FIG. 1A. The frame 102 comprises a bioabsorbable material. The compliance of the frame increases along the first direction as the bioabsorbable material is absorbed, for example within a body vessel, after passage of a period of time 140. Upon absorption of the bioabsorbable material after implantation in the body vessel, the medical device 100 has a first compliance 190. As shown in FIG. 1B, which shows an end view of the device at a first time shown in FIG. 1A, the first compliance is demonstrated by a first displacement 120 in response to a force 112 that is applied along a first direction 108. The force 112 could also be applied along a second direction 106 to measure a second displacement that is indicative of a second compliance. The compliance of a frame may be the same or different along different directions, depending on the particular embodiment being described.

Figure 1C:
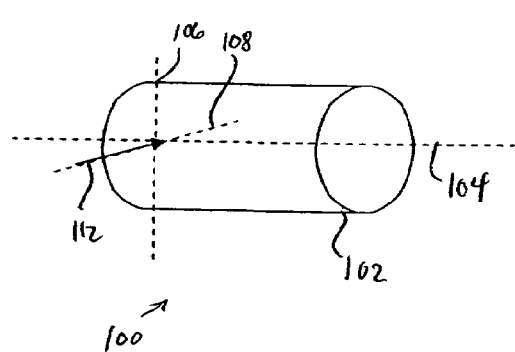
FIG. 1C is a schematic and FIG. 1D is a cross-sectional view of a second medical device having a second, increased, compliance in the first direction.
Figure 1D:
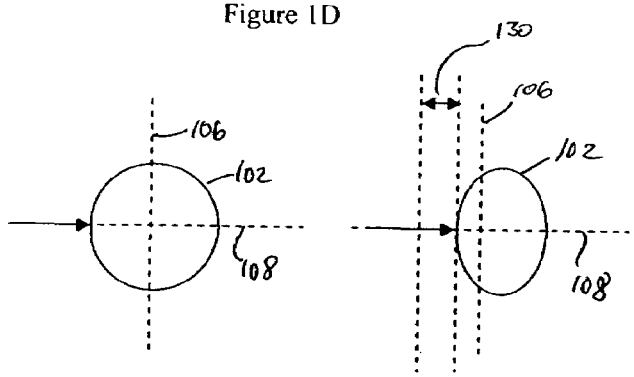

FIG. 1C shows the medical device frame 102 of FIG. 1A and FIG. 1B after the passage of time such that the bioabsorbable material has been substantially absorbed. As a result of absorption of the bioabsorbable material, the medical device 100 at a second time has a second compliance that is greater than the first compliance of FIGS. 1A-1B at the first time. As shown in the end view of FIG. 1D, which shows the same medical device of FIG. 1C, the second compliance is demonstrated by a second displacement 130 in response to the force 112 that is applied along the first direction 108. Applying the same force 112 to the frame with the second compliance of FIGS. 1C-1D at the second time 150 results in a larger second displacement 130 than the first displacement 120 of the frame with the first compliance.

Suitable support frames can have a variety of configurations, including braided strands, helically wound strands, ring members, consecutively attached ring members, tube members, and frames cut from solid tubes. Also, suitable frames can have a variety of sizes. The exact configuration and size chosen will depend on several factors, including the desired delivery technique, the nature of the vessel in which the device will be implanted, and the size of the vessel. A frame structure and configuration can be chosen to facilitate maintenance of the device in the vessel following implantation.

The dimensions of the implantable frame will depend on its intended use. Typically, the implantable frame will have a length in the range from 0.5 cm to 10 cm, usually being from about 1 cm to 5 cm, for vascular applications. The small (radially collapsed) diameter of a cylindrical frame will usually be in the range from about 1 mm to 10 mm, more usually being in the range from 1.5 mm to 6 mm for vascular applications. The expanded diameter will usually be in the range from about 2 mm to 30 mm, preferably being in the range from about 2.5 mm to 15 mm for vascular applications. The body segments may be formed from conventional malleable materials used for body lumen stents and grafts, typically being formed from metals.

The frame can comprise a plurality of struts. Struts are structures that can resist longitudinal compression. Struts can be an identifiable segment of an elongated frame member, for example separated by bends in the member, individual segments joined together, or any combination thereof. Struts can have any suitable structure or orientation to allow the frame to provide a particular compressibility, expandability, or any combination thereof. For example, struts can be oriented substantially parallel to, substantially perpendicular to, or diagonal to the longitudinal axis of a tubular frame, or some combination thereof. Struts can be straight or arcuate in shape, and can be joined by any suitable method, or can form one or more distinct rings.

Struts can be formed by folding a continuous member, or be joined by soldering, welding, or other methods to join ends. Besides joining strut segments, the frame could be fabricated as a single piece of material, by stamping or cutting the frame from another sheet (e.g., with a laser), fabricating from a mold, or some similar method of producing a unitary frame. Optionally, bioabsorbable materials can be incorporated in the frame by any suitable method, including directly fabricating the frame from the bioabsorbable material, or coating one or more bioabsorbable materials onto each other or onto another material. Bioabsorbable struts can be joined to non-bioabsorbable struts by any suitable method.

In one embodiment, the frame comprises a plurality of struts connected by alternating bends. For example, in one embodiment, the frame can be an annular ring member comprising a series of struts in a "zig-zag" pattern. In some embodiments, the struts are substantially aligned along the surface of a tubular plane, substantially parallel to the longitudinal axis of the support frame.

The frame can, in some embodiments, have a non-uniform density of struts. For example, the frame can comprise a first circumferential region having continuously joined regions of a first and a second strut density per unit of circumferential distance which intersect the first and second radial directions, respectively.

Measuring Reduction of Frame Compliance

The compliance of a frame can preferably be reduced by a compliance reducing test outside a body vessel, or by implantation within a body vessel. A compliance reducing test refers to subjecting the frame to any environment for a time period sufficient to reduce the compliance of the frame. Preferably, a compliance reducing test subjects the frame to test conditions that simulate one or more conditions within a body vessel after implantation that promote the reduction in compliance of the frame within the body vessel. In one aspect, a frame is subjected to compliance reducing test conditions ("test conditions") of mechanical stress or a chemical environment, or combination thereof, such that a reduction in compliance under test conditions is predictive of a reduction in compliance upon implantation in a body vessel. Examples of test conditions include mechanical fatigue testing and biochemical reactor conditions. Preferably, a frame is initially characterized by a first compliance measurement prior to subjecting the frame to a test condition that reduces the compliance, and the frame is subsequently characterized by a second compliance measurement after exposure to the test condition. Preferably, the first compliance measurement and the second compliance measurement are comparable. For example, both compliance measurements can be obtained using the same a Radial Force Gauge and compliance measurement protocol.

In one embodiment, the test conditions are a type of mechanical fatigue testing. For example, conditions of temperature, pressure, biochemical exposure, and mechanical loading or movement found within a body vessel can be simulated the Flat Plate Fatigue Test. A Flat Plate Fatigue Test is a preferred mechanical fatigue test. Other mechanical fatigue tests include variations of the Flat Plate Fatigue Test. The flat plate fatigue apparatus can comprise a first plate maintained parallel to a second plate that are adapted to be translated in rapid oscillation with respect to each other. The tubular frame is placed in a flexible (e.g., silicone-based) tube, to form a frame-tube assembly that is securely positioned between the first plate and the second plate. The flat plate fatigue apparatus is positioned within a fluid-containing cell that allows for immersing the frame in a fluid.

When performing the Flat Plate Fatigue Test, a fluid flow of phosphate-buffered saline at about 37° C. is preferably maintained within the flexible tube, passing through the frame. The maximum distance between the first plate and the second plate is set to maintain each plate in parallel and in contact with the flexible tube during the testing. During the Flat Plate Fatigue Test, the frame and the flexible tube are cyclically compressed between the first plate and the second plate for a compression of about 10% of the diameter of the uncompressed frame, at a rate of about 30 Hz for about 9 hours.

In other embodiments, other mechanical fatigue tests can be performed as compliance reducing test conditions that simulate conditions within a body vessel. For example, a frame can be tested in a test similar to the Flat Plate Fatigue test, where the frame is not exposed to a fluid. Alternatively, a frame may be exposed to a fluid with certain biochemically active properties, such as the presence of enzymes. A fluid may have a particular pH range, for example to simulate pH conditions in portions of the gastrointestinal, urinary or bile tracts. The fluid may comprise whole blood or any compositions thereof, derived from any suitable source such as bovine or porcine sources. Various cycling rates may also be used, such as ranges of about 10 Hz to about 50 Hz. Also, the amount of compression of the frame may be varied, for example from about 1% to about 25% of the non-compressed diameter. The temperature of the frame or a fluid contacting the frame may be varied as well, but preferably simulates the temperature within a body vessel (about 37° C. for humans). The number of oscillation cycles of the frame by movement of the flat plates can be varied to any suitable number. The number of cycles will depend on the intended use.

Frames can be designed to reduce compliance after an intended period of time. For a frame designed to undergo a reduction in compliance after about 6 months within a vein, about one million cycles at 30 Hz is preferred. Within the lumen of a vein in the human leg, an implanted frame is believed to undergo an estimated 5,000 oscillations per day. In one aspect, an SIS remodelable material is attached to a frame for implantation in a vein. In this environment, SIS is expected to remodel within about 6 months. Accordingly, the frame for such an application desirably loses compliance after the number of oscillations equivalent to 6 months in a vein, or about 900,000 to one million oscillations. At an oscillation rate of about 30 Hz, the frame should undergo a reduction in compliance after about 8.3 hours. Accordingly, the frame should have a first compliance before the mechanical fatigue testing, and a reduced compliance measured after about 9 hours of mechanical fatigue testing.

Frames can also be exposed to biochemical conditions that reduce the compliance. For example, the frame can be contacted with living tissue, or placed in a bioreactor that simulates biochemical conditions within a body vessel. In one embodiment, the frame is subjected to a Blood Component Contact test, where the frame is contacted with blood for a period sufficient to reduce the compliance of the frame, such as 30, 60, or 90 days. The blood for the Blood Contact Test can be obtained from a suitable source, such as bovine or porcine sources. Any suitable test can be used to simulate one or more conditions typically found within a body vessel where the frame is intended for implantation. For example, a frame comprising a bioabsorbable polymer can be exposed to conditions that promote the dissolution of the bioabsorbable polymer to an extent present after a desired period of implantation in a body vessel. The test conditions can be calibrated to expose the frame to conditions that cause the reduction of the frame within the body vessel, such as pH, temperature, or presence of particular bioactive blood components.

Preferably, a medical device for implantation in a body vessel comprising a frame is characterized by a first compliance measurement prior to conducting a compliance reducing test, and a second compliance measurement after conducting the compliance reducing test, where the first compliance and the second compliance are measured by a Radial Force Gauge; and the second compliance measurement is less than the first compliance measurement. More preferably, the compliance reducing test is a Flat Plate Fatigue Test.

The radial strength of a frame is preferably measured using a Radial Force Gauge. One preferred Radial Force Gauge the RX600 Radial Expansion Force Gage equipment from Machine Solutions Inc. (MSI). A Radial Force Gauge measures the radial strength of both balloon expandable and self-expanding stent and stent graft products during expansion and compression. The RX600 equipment uses a segmental compression mechanism controlled by a micro-stepping linear actuator that is designed to provide an extremely low friction testing environment. Preferably, the Radial Force Gauge maintains resolution at force levels from 0 to 80 Newtons, for example using a software-controlled interchangeable linear force transducer, or other suitable means. The Radial Force Gauge preferably measures the hoop strength of the frame.

Optionally, the Radial Force Gauge allows the hoop strength of the frame to be visualized and recorded as the product is cycled through programmed open and close diameters.

Implantable Frame Materials

Frames can be constructed of any suitable material. Examples of suitable materials include, without limitation: stainless steel, nickel titanium (NiTi) alloys (such as Nitinol) and other shape memory and/or superelastic materials, MP35N, gold, tantalum, platinum or platinum iridium, a cobalt-chromium alloy or other biocompatible metals and/or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhidride, polyether sulfone, polycarbonate, polypropylene, high molecular weight polyethylene, polytetrafluoroethylene, or other biocompatible polymeric material, or mixture of copolymers thereof, or stainless steel, polymers, and any suitable composite material.

Preferably, the frame can have compressed and expanded configurations. In some embodiments, the expanded configurations can be resiliently further extended in one or more radial directions. In some embodiments, a frame can expand from a compressed, or unexpanded, delivery configuration to one or more radially expanded deployment configurations, for example through self expansion or balloon expansion of the frame. The expanded configuration can have any suitable cross-sectional configuration, including circular or elliptical. In one embodiment, the frame can be oriented along the longitudinal axis of a body vessel in the expanded or compressed configurations.

In one embodiment, the frame is self-expanding. Upon compression, self-expanding frames can expand toward their pre-compression geometry. In some embodiments, a self-expanding frame can be compressed into a low-profile delivery conformation and then constrained within a delivery system for delivery to a point of treatment in the lumen of a body vessel. At the point of treatment, the self-expanding frame can be released and allowed to subsequently expand to another configuration. In certain embodiments, the frame is formed partially or completely of alloys such as nitinol (NiTi) which have superelastic (SE) characteristics.

In some embodiments, the frame comprises a superelastic material. Materials having superelastic properties generally have at least two phases: a martensitic phase, which has a relatively low tensile strength and which is stable at relatively low temperatures, and an austenitic phase, which has a relatively high tensile strength and which can be stable at temperatures higher than the martensitic phase. Shape memory alloys undergo a transition between an austenitic phase and a martensitic phase at certain temperatures. When they are deformed while in the martensitic phase, they retain this deformation as long as they remain in the same phase, but revert to their original configuration when they are heated to a transition temperature, at which time they transform to their austenitic phase. The temperatures at which these transitions occur are affected by the nature of the alloy and the condition of the material. Nickel-titanium-based alloys (NiTi), wherein the transition temperature is slightly lower than body temperature, are preferred for the present invention. It can be desirable to have the transition temperature set at just below body temperature to insure a rapid transition from the martinsitic state to the austenitic state when the frame can be implanted in a body lumen.

For example, a nitinol frame can be deformed by collapsing the frame and creating stress which causes the NiTi to reversibly change to the martensitic phase. The frame can be restrained in the deformed condition inside a delivery sheath typically to facilitate the insertion into a patient's body, with such deformation causing the isothermal phase transformation. Once within the body lumen, the restraint on the frame can be removed, thereby reducing the stress thereon so that the superelastic frame returns towards its original undeformed shape through isothermal transformation back to the austenitic phase.

A NiTi alloy structure, such as NITINOL™, is preferably compressed to facilitate its insertion into a body lumen or cavity, and then heated within the body so that the structure returns to its original, expanded shape.

In some embodiments, a shape memory effect can be imparted to an alloy useful in constructing a self-expanding frame by heating the nickel-titanium metal to a temperature above which the transformation from the martensitic phase to the austenitic phase can be complete; i.e., a temperature above which the austenitic phase can be stable. The shape of the metal during this heat treatment can be the shape "remembered." The heat-treated metal can be cooled to a temperature at which the martensitic phase can be stable, causing the austenitic phase to transform to the martensitic phase. The metal in the martensitic phase can be then plastically deformed, e.g., to facilitate the entry thereof into a patient's body. Subsequent heating of the deformed martensitic phase to a temperature above the martensitic to austenitic transformation temperature causes the deformed martensitic phase to transform to the austenitic phase. During this phase transformation the metal reverts back towards its original shape.

The recovery or transition temperature can be altered by making minor variations in the composition of the metal and in processing the material. In developing the correct composition, biological temperature compatibility must be determined in order to select the correct transition temperature. In other words, when the frame can be heated, it must not be so hot that it can be incompatible with the surrounding body tissue. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," Scientific American, 281: 74-82 (November 1979), incorporated herein by reference.

However, while some embodiments provide frames made from shape memory materials, other embodiments comprise other materials. Some embodiments provide frames that are not self-expanding, or that do not comprise superelastic materials. Some frames are balloon expandable.

The frame can include structural features, such as barbs, that maintain the frame in position following implantation in a body vessel. The art provides a wide variety of structural features that are acceptable for use in the medical device, and any suitable structural feature can be used. Furthermore, barbs can also comprise separate members attached to the frame by suitable attachment means, such as welding and bonding. For instance, barbs can be formed by V-shaped cuts transversing the thickness of a flat metal frame, which are bent outward to form the barb. In some embodiments, the number, arrangement, and configuration of the integral barbs can vary according to design preference and the clinical use of the device. The barbs can have any suitable shape, including points or "fish hook"-like configurations. The barbs may or may not penetrate the vein wall, depending on their design and other factors, including the thickness and type of covering used.

Also provided are embodiments wherein the frame comprises a means for orienting the frame within a body lumen. For example, the frame can comprise a marker, such as a radiopaque portion of the frame that would be seen by remote imaging methods including X-ray, ultrasound, Magnetic Resonance Imaging and the like, or by detecting a signal from or corresponding to the marker. In other embodiments, the delivery device can comprise a frame with indicia relating to the orientation of the frame within the body vessel. In other embodiments, indicia can be located, for example, on a portion of a delivery catheter that can be correlated to the location of the frame within a body vessel.

A frame or delivery device may comprise one or more radiopaque materials to facilitate tracking and positioning of the medical device, which may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platium, iridium, and rhodium. In one preferred embodiment, iodine may be employed for its radiopacity and antimicrobial properties. Radiopacity is typically determined by fluoroscope or x-ray film.

In one preferred embodiment, iodine may be employed for its radiopacity and antimicrobial properties. Radiopacity is typically determined by fluoroscope or x-ray film. Various other ways to incorporate radiopaque material in a medical device are provided in copending application Ser. No. 10/787,307, filed Feb. 26, 2004 by Case et al., entitled "Prosthesis Adapted for Placement Under External Imaging," which is incorporated herein by reference. Imagable markers, including radiopaque material, can be incorporated in any portion of a medical device. For example, radiopaque markers can be used to identify a long axis or a short axis of a medical device within a body vessel. For instance, radiopaque material may be attached to a frame or woven into portions of the valve member material.

Implantable Frames Comprising Bioabsorbable Materials

A medical device can comprise one or more bioabsorbable materials. As used herein, "bioabsorbable polymer" refers to a polymer or copolymer which is absorbed by the body. A large number of different types of materials are known in the art which may be inserted within the body and later dissipate. The term "bioabsorbable" is used herein to refer to materials selected to dissipate upon implantation within a body, independent of which mechanisms by which dissipation can occur, such as dissolution, degradation, absorption and excretion. The actual choice of which type of materials to use may readily be made by one ordinarily skilled in the art. Such materials are often referred to by different terms in the art depending upon the mechanism by which the material dissipates, as "bioresorbable," "bioabsorbable," or "biodegradable." The prefix "bio" indicates that the erosion occurs under physiological conditions, as opposed to other erosion processes, caused for example, by high temperature, strong acids or bases, UV light or weather conditions.

The terms "absorption," "bioresorption" and "bioabsorption" can be used interchangeably herein to refer to the ability of the polymer or its degradation products to be removed by biological events, such as by fluid transport away from the site of implantation or by cellular activity (e.g., phagocytosis). There may be some discussion among those skilled in the art as to the precise meaning and function of bioabsorbable materials, and how they differ from resorbable, absorbable, bioresorbable, and biodegradable, the current disclosure contemplates all of these materials as "bioabsorbable" materials. Still, the aforementioned terminology is widely used interchangeably by medical professionals. Accordingly, and for conciseness of presentation, only the term "bioabsorbable" will generally be used in the following description to encompass resorbable, absorbable, bioresorbable, and biodegradable, without implying the exclusion of the other classes of materials.

A "biocompatible" material is a material that is compatible with living tissue or a living system by not being toxic or injurious and not causing immunological rejection.

"Non-bioabsorbable" material refers to a material, such as a polymer or copolymer, which remains in the body without substantial bioabsorption.

A bioabsorbable material can be selected from any number of bioabsorbable homopolymers, copolymers, or blends of bioabsorbable polymers. In some embodiments, a medical device frame can comprise a biocompatible, bioabsorbable polymer or copolymer, a synthetic, biocompatible, non-bioabsorbable polymer or copolymer, or combinations thereof.

Figure 2A:
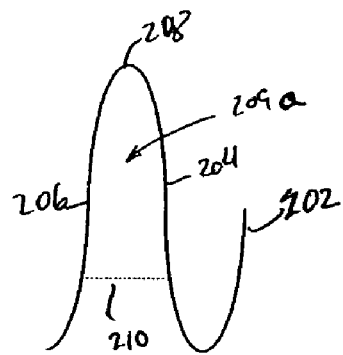
FIG. 2A, FIG. 2B, and FIG. 2C are diagrams of a portion of different frames comprising struts, bends and a support arm.
Figure 2B:
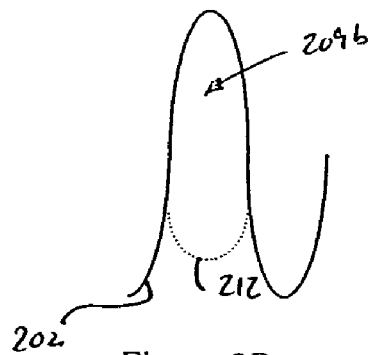
Figure 2C:
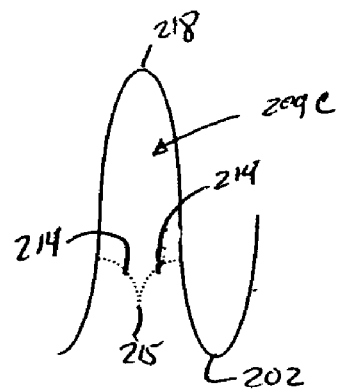

FIGS. 2A-2E show portions of frames comprising struts that include a bioabsorbable material. FIG. 2A, FIG. 2B, and FIG. 2C are diagrams of a portion of different frames comprising two struts, a bend and a support arm. Portions of a first type of frame 200 are shown in FIG. 2A, FIG. 2B, and FIG. 2C, each comprising a frame member segment 202 bent in a sinusoidal fashion. As exemplified by FIG. 2A, the frame member segment 202 comprises a first strut 204 joined to a second strut 206 by a bend 208. In one embodiment, the first frame can continue in either direction from the portion shown, and one end of the frame can be folded over and joined to the opposite end to form an annular ring-shaped frame.

The frame can optionally comprise one or more support arms. Support arms can be members joining one or more portions of the frame and can be in any suitable geometric configuration, including straight or curved. The bioabsorption or fracture of a support arm increases the compliance of the frame in at least one direction. For example, in some embodiments, support arms can fracture under a lesser mechanical load than the other portions of the frame, or the support arms can comprise a bioabsorbable material that, when absorbed, increases the compliance of the frame.

FIG. 2A, FIG. 2B, and FIG. 2C show three non-limiting examples of different types of support arms that can be used. The illustrated embodiments of FIG. 2A, FIG. 2B, and FIG. 2C illustrate only a portion of a frame that can be repeated on either side of the frame segment shown. The struts of the frame member segment 202 can optionally be joined by one or more support arms. In FIG. 2A, a first support arm 210 is a substantially straight segment of bioabsorbable material joining the first strut 204 and the second strut 206. Upon implantation, the first type of support arm 210 is gradually absorbed in vivo until it falls away from the frame, thereby increasing the compliance of the member 202. A first frame opening 209a is defined by the support arm 210 and the frame member segment 202. In FIG. 2B, a second type of support arm 212, which has an arcuate shape, is also shown joining two other struts. The second type of support arm 212 comprises a core material that is not bioabsorbable, surrounded by an outer layer of a bioabsorbable material. When the bioabsorbable external material is absorbed, the diameter of the second type of support arm 212 decreases, increasing the compliance of the frame member segment 202, for example by allowing the a bend to bend inward more easily. A second frame opening 209b, defined by the support arm 212 and a portion of the frame member segment 202, grows smaller as the diameter of the support arm 212 decreases. A third type of support arm 214 is shown in FIG. 2C, which has a tent-like arcuate structure, and is designed to fracture at its central apex joint 215 in response to excessive stress compressing the third bend 218. For example, fracture of the third type of support arm 214 could prevent damage to a body vessel that compresses the frame by decreasing the resistance of the frame. Although the illustrated embodiments provide a single support arm between two struts, other embodiments providing multiple support arms attached to a single strut are also included in the invention. A third frame opening 209c is defined by the support arm 214 and the frame member segment 202. While the illustrated embodiments of FIG. 2A, FIG. 2B, and FIG. 2C do not show support arms across the adjacent frame opening on the right of the opening with the support arm, support arms can also be provided across consecutive frame openings defined by two struts and a bend.

Figure 2D:
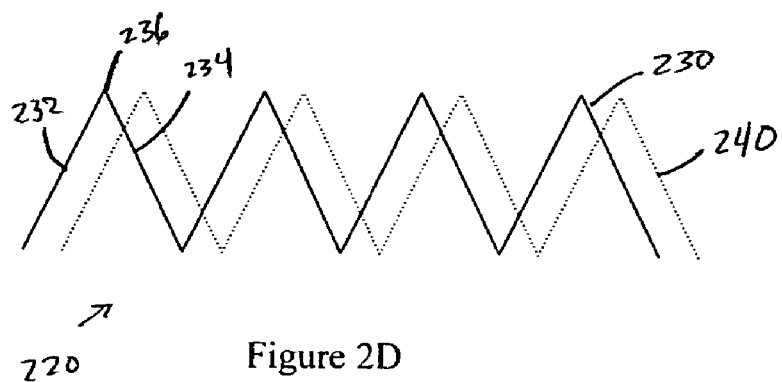
FIG. 2D and FIG. 2E are diagrams of portions of other frame structures.
Figure 2E:
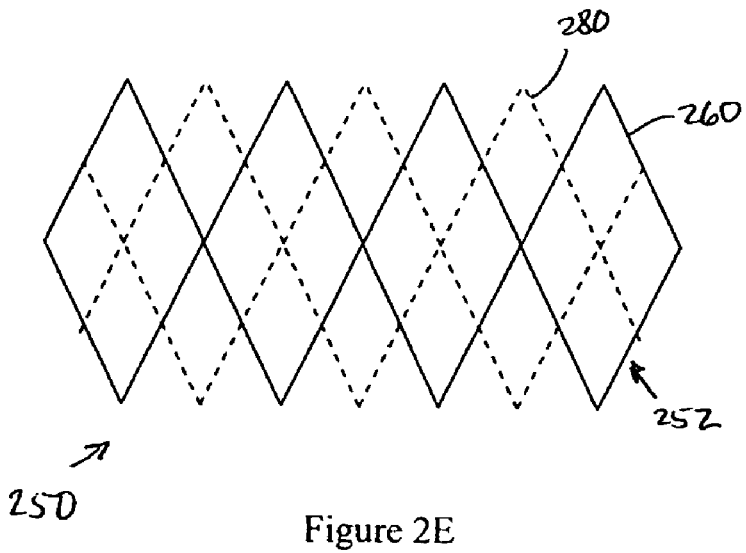

As shown in FIG. 2D, a second type of frame 220 comprises a first member 230 that is non-bioabsorbable joined to a second member 240 that is bioabsorbable. Each member is formed into a "zig zag" fashion to define a series of struts joined by bends. For example, the first member 230 comprises a first strut 232 and a second strut 234 joined by a first bend 236. The struts may be joined in any suitable fashion known in the art. As shown in FIG. 2E, a third type of frame 250 comprises a first member array 260 of bioabsorbable material joined to a second member array 280 that is not bioabsorbable. Each member array is made from two or more "zig-zag"-shaped members joined to form an array of diamond-shaped cells.

Several bioabsorbable, biocompatible polymers have been developed for use in medical devices, and approved for use by the U.S. Food and Drug Administration (FDA) that are suitable for use in medical device implantable frames herein. These FDA-approved materials include polyglycolic acid (PGA), polylactic acid (PLA), Polyglactin 910 (comprising a 9:1 ratio of glycolide per lactide unit, and known also as VICRYL™), polyglyconate (comprising a 9:1 ratio of glycolide per trimethylene carbonate unit, and known also as MAXON™), and polydioxanone (PDS). In general, these materials biodegrade in vivo in a matter of months, although some more crystalline forms can biodegrade more slowly. These materials have been used in orthopedic applications, wound healing applications, and extensively in sutures after processing into fibers. More recently, some of these polymers also have been used in tissue engineering applications.

A variety of bioabsorbable and biocompatible materials can be used to make medical device frames useful with particular embodiments disclosed herein, depending on the combination of properties desired. Properties such as flexibility, compliance, and rate of bioabsorption can be selected by choosing appropriate bioabsorbable materials. The properties of the bioabsorbable polymers may differ considerably depending on the nature and amounts of the comonomers, if any, employed and/or the polymerization procedures used in preparing the polymers.

For instance, bioabsorbable biocompatible polymers can provide flexible, elastomeric properties, for example by incorporating lactide or glycolide and caprolactone joined by a lysine-based diisocyante into a polyurethane (Lamba, et al., "Degradation of Polyurethanes" in Polyurethanes in Biomedical Applications, pp. 199-200 (CRC Press LLC, Boca Raton, Fla., 1998). The polyurethane segments are not believed to completely biodegrade in vivo. A commercial material, known as TONE™, has also been evaluated as an elastomeric implant material that degrades more slowly in vivo (Perrin, et al., "Polycaprolactone" in Handbook of Bioabsorbable Polymers (Domb, et al., eds.) pp. 63-76 (Harwood, Amsterdam, 1997)). Other bioabsorbable materials can be synthesized from protein-based polymers, particularly polymers containing elastomeric polypeptide sequences (Wong, et al., "Synthesis and properties of bioabsorbable polymers used as synthetic matrices for tissue engineering" in Synthetic Bioabsorbable Polymer Scaffolds (Atala & Mooney, eds.) pp. 51-82 (Birkhauser, Boston, 1997). Cells can invade matrices derived from these materials. U.S. Pat. Nos. 5,468,253 and 5,713,920, both to Bezwada et al., disclose other bioabsorbable elastomeric materials which are used to form devices that, based on in vitro data, are alleged to completely bioabsorb within one year or six months.

Other useful biocompatible frame materials include those disclosed in U.S. Pat. No. 4,838,267, for example, including block copolymers derived from p-dioxanone and glycolide that exhibit a high order of initial strength and compliance but lose their strength rapidly after implantation in the body. Sutures made from the copolymers are said to be particularly useful in surgical procedures, such as plastic surgery or repair of facial wounds, where it is desirable for the suture to lose its strength rapidly. U.S. Pat. Nos. 4,605,730 and 4,700,704 disclose copolymers of epsilon-caprolactone and glycolide useful in making surgical articles and particularly surgical sutures having low Young's modulus. In addition, U.S. Pat. No. 4,624,256 relates to the utilization of high molecular weight caprolactone polymers as coatings for surgical sutures, while U.S. Pat. No. 4,429,080 discloses surgical articles manufactured from triblock copolymers prepared from copolymerizing glycolide with trimethylene carbonate.

In some embodiments, the bioresorbable material of the frame can degrade, post implantation, at a rate that allows for remodeling of remodelable material attached to the frame. A variety of resorbable, biocompatible materials, for example polymers, may be employed for manufacturing a suitable frame for implantation for such an embodiment. Homopolymers and copolymers such as those disclosed in U.S. Pat. No. 5,412,068, incorporated herein by reference, are appropriate for the resorbable frames of the present invention. Particular bioresorbable materials may be chosen to fit particular patient needs. For example, polymers may be chosen to be bioabsorbed within any suitable time period, including a 7-21 day interval, a 2-4 week interval, a 3-6 week interval, a 6 to 8 week interval, a 1 to 3 month interval, a 2 to 4 month interval, a 3 to 6 month interval or a 4-8-month interval, but other polymers may be chosen to be bioabsorbed within shorter or longer intervals. Variations in selected times to bioabsorption may depend on, for example, the overall health of the patient, variations in anticipated immune reactions of the patient to the implant, the site of implantation, and other clinical indicia apparent to the skilled artisan.

Bioabsorbable polymers that could be used include polymers selected from the group consisting of polyesters, poly (amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, poly-hydroxy acids, trimethlyene carbonate, poly-beta-hydroxy acids, polyorganophosphazines, polyanhydrides, polyesteramides, polyethylene oxide, polyester-ethers, polyphosphoester, polyphosphoester urethane, cyanoacrylates, poly(trimethylene carbonate), poly(iminocarbonate), polyalkylene oxalates, polyvinylpyrolidone, polyvinyl alcohol, poly-N-(2-hydroxypropyl)-methacrylamide, polyglycols, aliphatic polyesters, poly(orthoesters), poly(ester-amides) and polyanhydrides.

Still more specifically, in one embodiment, the bioabsorbable material may comprise, without limitation, a polyester, poly(hydroxy acids) and copolymers thereof, poly(epsilon-caprolactone), poly(dimethyl glycolic acid) and poly(hydroxy butyrate). In another embodiment, the bioabsorbable material can be a poly(lactide), poly(glycolide), poly(p-dioxanone), and co-polymers thereof. In another embodiment, the bioabsorbable material comprises a polyester-ethers such as polydioxanone, or a copoly(ether-esters) such as PEO/PLA.

In some embodiments, the bioabsorbable material can comprise any bioabsorbable co-polymer of known bioabsorbable materials, including without limitation, poly(lactide-co-glycolide), poly(hydroxybutyrate-co-valerate), poly(glycolic acid-co-trimethylene carbonate), poly(epsilon-caprolactone-co-p-dioxanone), poly(lactide-co-glycolide), poly-L-glutamic acid or poly-L-lysine.

In one embodiment, the bioabsorbable material comprises a poly-alpha-hydroxy acid such as polylactic acid, polylactide, polyglycolic acid, or polyglycolide. Preferably, the bioabsorbable material can comprise poly(D,L-lactic acid), L-polylactic acid, or glycolic acid, or copolymers of D,L-polylactic acid, L-polylactic acid, and glycolic acid. Such polymers may be manufactured and configured as disclosed, for example, in U.S. Pat. No. 5,133,755, incorporated by reference herein. In one embodiment, the bioabsorbable material comprises a poly-beta-hydroxy acid such as polyhydroxybutyrate or polyhydroxyvalerate.

Bioabsorbable materials further include modified polysaccharides (such as cellulose, chitin, and dextran), modified proteins (such as fibrin and casein), fibrinogen, starch, collagen and hyaluronic acid. The bioabsorbable material may also be, without limitation, hydroxyethyl starch, gelatin, and derivatives of gelatin.

References in the art can be consulted to determine the properties and preparation of bioabsorbable materials. Preparation of these and other biocompatible bioabsorbable polymers or copolymers are known in the art. For example, disclosures of U.S. Pat. Nos. 5,705,181 and 5,393,594, relate to the preparation and use poly(lactide), poly(glycolide), poly(epsilon-caprolactone), poly(p-dioxanone), poly(epsilon-caprolactone-co-p-dioxanone) and poly(lactide-co-glycolide). U.S. Pat. No. 5,522,841, incorporated herein by reference, relates to the preparation and use of bioabsorbable block copolymers made of hard phase forming monomers, e.g., glycolide and lactide, and soft phase monomers, e.g., 1,4 dioxane-2-one and caprolactone, as described. Bioabsorbable polymers derived in whole or in part from dioxanone can be used in some embodiments. Homopolymers of p-dioxanone are described, e.g., in U.S. Pat. Nos. 3,063,967; 3,063,968; 3,391,126; 3,645,941; 4,052,988; 4,440,789; and, 4,591,630. Copolymers containing units derived from p-dioxanone and one or more other monomers that are copolymerizable therewith are described, e.g., in U.S. Pat. Nos. 4,243,775; 4,300,565; 4,559,945; 4,591,630; 4,643,191; 4,549,921; 4,653,497; 4,791,929; 4,838,267; 5,007,923; 5,047,048; 4,076,807; 5,080,665; and 5,100,433 and European Patent Application Nos. 501,844 and 460,428.

Further relevant references can include, for example, D. K. Gilding et al., "Biodegradable polymers for use in surgery-polyglycolic/poly(lactic acid) homo- and copolymers: 1," Polymer, 20: 1459-1464 (1979), and D. F. Williams (ed.), Biocompatibility of Clinical Implant Materials, Volume II, chapter 9: "Biodegradable Polymers" (1981), which are incorporated herein by reference. Polymers, copolymers and devices made from ϵ-caprolactone and/or related compounds have also been described in U.S. Pat. Nos. 3,169,945, 3,912,692, 3,942,532, 4,605,730, 4,624,256, 4,643,734, 4,700,704, 4,788,979, 4,791,929, 4,994,074, 5,076,807, 5,080,665, 5,085,629 and 5,100,433.

Variations in selected times for bioabsorption may depend on, for example, the overall health of the patient, variations in anticipated immune reactions of the patient to the implant, the site of implantation, and other clinical indicia apparent to the skilled artisan. Bioabsorbable materials may be selected to form at least a portion of a frame so as to provide an increased frame compliance after a particular period of time, for example as discussed in the references herein. In certain embodiments, bioabsorption of a biomaterial in a frame can increase the compliance of the frame in a first direction. In some embodiments, the frame may be designed to bend radially inward in response to a pressure.

In one embodiment, the frame can further comprise a first bioabsorbable material or a non-bioabsorbable material as a "core" material. The core material can be at least partially enclosed by a second bioabsorbable material. The frame can also comprise a surface area presenting both a bioabsorbable material and a non-bioabsorbable material, and absorption of the bioabsorbable material can increase the surface area, resulting in an increase of the compliance of the frame in a first direction. The frame can further include one or more support arms comprising a bioabsorbable material, and absorption of the bioabsorbable material can increase the compliance of the frame in the first direction.

In another embodiment, the frame comprises a nonabsorbable polymer. Examples of synthetic biocompatible non-bioabsorbable polymers include, but are not limited to, homopolymers and copolymers of polypropylene, polyamides, polyvinylchlorides, polysulfones, polyurethanes, polytetrafluoroethylene, ethylene vinyl acetate (EVAC), polybutylmethacrylate (PBMA) or methylmethacrylate (MMA). The frame can comprise the non-absorbable polymer in amounts from about 0.5 to about 99% of the final composition. The addition of EVAC, PBMA or methylmethacrylate increases malleability of the matrix so that the device is more plastically deformable. Various constructs of the elongate elements, fibers and threads can be formed utilizing well known techniques, e.g., braiding, plying, knitting, weaving, that are applied to processing natural fibers, e.g., cotton, silk, etc., and synthetic fibers made from synthetic bioabsorbable polymers, e.g., poly(glycolide) and poly(lactic acid), nylon, cellulose acetate, etc. See, e.g., Mohamed, American Scienitist, 78: 530-541 (1990). Specifically, collagen thread is wound onto cylindrical stainless steel spools. The spools are then mounted onto the braiding carousel, and the collagen thread is then assembled in accordance with the instructions provided with the braiding machine. In one particular run, a braid was formed of four collagen threads, which consisted of two threads of uncrosslinked collagen and two threads of crosslinked collagen.

FIG. 3A is a diagram, and FIG. 3B is a corresponding cross section, of a portion of a frame comprising a non-bioabsorbable core material surrounded by a bioabsorbable material. Bioabsorption of the bioabsorbable material increases the compliance of the frame. The first frame shown in FIG. 3A, and a cross section along 3B-3B is shown in FIG. 3B. The first frame comprises a first frame member 302 (only a portion of which is shown) having a sinusoidal shape comprising a plurality of struts connected by bends. The cross section of the first frame in FIG. 3B along 3B-3B shows that the first frame member 302 has a core layer 320 that is not bioabsorbable, surrounded by an outer layer 310 that is bioabsorbable. When implanted in a body vessel, the outer layer 310 is gradually bioabsorbed, thereby increasing the flexibility of the first frame member 302 and the compliance of the first frame 300. The first frame can be folded into a ring by joining the ends of the first frame member 302. Optionally, multiple such ring structures can be stacked end-to-end to form a more elongated tubular frame.

A second frame shown in FIGS. 3C-3E is formed from a sinusoidal second frame member 352 that is bent to form a plurality of struts joined by a plurality of bends. A cross section of the second frame member 352 in FIG. 3D taken along 3D-3D shows that the second frame member 352 has a core layer 360 that is not bioabsorbable. The core layer 360 has a series of indentations along the surface, such as grooves or pits, that are filled with a bioabsorbable material 364. FIG. 3E is a detail view of a surface portion of the cross section of the second frame member 352 shown in FIG. 3D. FIG. 3E shows bioabsorbable material 364 deposited in pits or grooves in the surface of the core material, separated by portions of the core material 362 defining the pits or grooves. Upon implantation, the bioabsorbable material 364 is bioabsorbed and the flexibility of the second frame member 352, along with the compliance of the second frame member 350, is gradually increased.

Figure 4A:
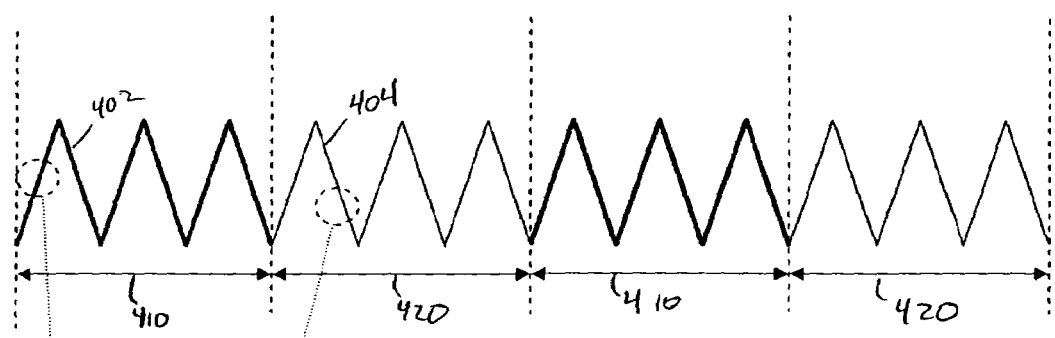
FIG. 4A is a diagram.
Figure 4B:
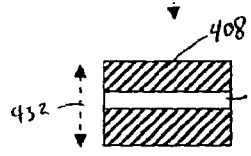
FIG. 4B and FIG. 4C are corresponding cross-sectional views, of a portion of a frame comprising struts with different cross-sectional dimensions.
Figure 4C:
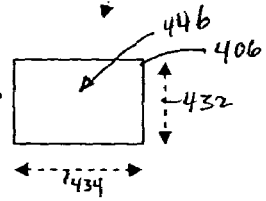

In another aspect, the shape or geometry of portions of one or more struts can be changed by the bioabsorption of material from the frame after implantation. FIGS. 4A-4D show a third frame member 402 comprising struts with different cross-sectional compositions. As shown in FIG. 4A, the struts comprise a bioabsorbable material 408, and a non-bioabsorbable material 406. The third frame member 402 has a "zig-zag"-shape frame having partially-bioabsorbable sections 410 joined to non-bioabsorbable sections 420. Alternating regions are formed from the partially bioabsorbable sections 410 and non-bioabsorbable sections 420. As illustrated in the cross section of FIG. 4B, the third frame member 402 in the partially-bioabsorbable sections 410 has a first cross section 430 and the second member 404 has a second cross section 440, with each cross section initially having a first dimension 432 and a second dimension 434 before implantation. Upon implantation, bioabsorption of the bioabsorbable material 408 decreases the first dimension but not the second dimension 434 of the first member 402, thereby increasing the compliance of the third frame member 402. FIG. 4C shows the cross section of a non-bioabsorbable section 420 of the third frame member 402.

Figure 4D:
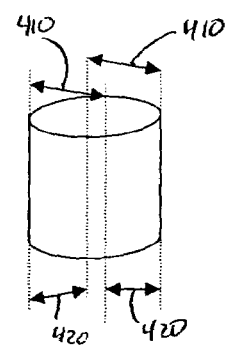
FIG. 4D is a perspective view of a tubular configuration of the frame.

As shown in FIG. 4D, the third frame member 402 can be formed in a tubular configuration 450 so that end portions of a partially bioabsorbable region 410 is joined to the end of a non-consecutive non-bioabsorbable region 420. The tubular configuration 450 can be assembled from the flat plane configuration of FIG. 4A. More preferably, the tubular configuration 450 can be formed directly by laser cutting holes a suitable cylindrical tube of frame material such as a NiTi alloy, to create the array of struts and bends desired. Each non-bioabsorbable section and likewise each bioabsorbable section can be composed of the same or of different materials, allowing compliance along the entire frame to vary.

FIGS. 5A-5E show other types of frames that can be used in certain embodiments. In one embodiment (FIG. 5A), a portion of a fourth frame 500 comprises a plurality of struts including a first strut 502 and a second strut 504 that are joined by insertion into a curved elbow section 506. The curved elbow 506 section forms a bend, and can be made from any material with an appropriate level of flexibility. One or more struts or elbows 506 can comprise a bioabsorbable material or a non-bioabsorbable material, a remodelable material, or any combination thereof. An elbow 506 can also be designed to partially fracture in response to force above a desired threshold level.

In another aspect (FIG. 5B), a portion of a fifth frame 510 comprises a first strut 512 and a second strut 514 joined by bend region 516. A portion of the frame is designed to fracture in a controlled fashion along a fracture line 518 by wrapping the bend region 516 with a binding material 517. When subjected to a compressive force pushing the first strut 512 and the second strut 514 toward each other, the frame will break at the point where the frame intersects the fracture line 518. When the frame breaks, the binding material 517 maintains the end of the first strut 512 and the end of the second strut 514 in close association, for example to prevent injury to an adjacent body vessel wall.

In addition to the curved "elbow"-like section and bends in a frame, other structures can be used to join struts. For example, as shown in FIG. 5C, a portion of a sixth frame 520 comprises a series of struts 522 joined by either a first bend 524 or a second bend 526. In some embodiments, the bends can be designed to bias the struts toward or away from one another. The first bend 524 is made from a coiled wire forming a tensioned spring that is joined to two struts 522. The coiled wire is one example of a bend that provides biasing of the struts toward or away from one another. The second bend 526 is a wire that is formed into a filet structure and joined to two struts 522. The filet structure can decrease the contact pressure of the bend against a vessel wall.

In yet another embodiment, shown in FIG. 5D, a portion of an eighth frame 530 can be formed from braiding together a first material 532 and a second material 534 and shaping the resulting structure into a sinusoidal frame comprising a first strut 536 and a second strut 538 joined by a bend 540. More than two materials can also be braided together in this fashion. A detail view of a portion of the eighth frame 530 is provided in FIG. 5E, showing the braiding of a first material 532 with a second material 534. For example, one or more bioabsorbable materials can be braided with one or more remodelable materials or non-bioabsorbable materials to provide a frame having a compliance that varies with time after implantation in a body vessel. In this embodiment, the first material 532 can be an SIS strip and the second material 534 can be a collagen strip that are braided and are dried together to form a support frame 530. By treating or coating the frame with a polymer as a temporary barrier to limit absorption of fluids which would degrade the frame, Upon implantation in a body vessel, the support frame 530 can retain rigidity for a period of time until the polymer starts to degrade or wear away, at which point the compliance of the frame can gradually increase with time.

In some embodiments, the compliance of the frame can be designed to increase after a period of time following implantation, and the compliance can change suddenly or gradually. The compliance of the frame can occur by various mechanisms. For example, the compliance of a frame comprising a bioabsorbable material can gradually increase with the bioabsorption of the bioabsorbable material after implantation. In another embodiment, the bioabsorption of a bioabsorbable support arm can result in a fracture of the arm in response to shear forces of blood flow, thereby suddenly increasing the compliance of the frame. In another embodiment, micro fractures in portions of the frame can increase the flexibility of portions of the frame, thereby increasing the compliance of the frame along a first direction.

The time period after implantation when the frame can increase compliance can, in some embodiments, be similar to the time period for bioabsorption of various bioabsorbable materials used to construct the frame. Other embodiments, provide a frame with a compliance that increases as a safety feature in response to a sudden pressure along a first direction so as to prevent damage to the lining of a body vessel. Still other embodiments provide a frame that increases compliance after a pre-determined period of implantation, for example, after about 30 days, about 2 weeks or about 1 week. In other embodiments, the frame can increase compliance after a longer period of time, such as 6 to 8 weeks.

Medical Devices Comprising Remodelable Materials

In a second embodiment, a medical device can comprise a frame and a remodelable material attached to the frame. Preferably, the frame maintains the remodelable material subject to a mechanical load adequate to allow remodeling of the remodelable material when the frame has the first compliance in the first direction.

Mechanical loading of remodelable material during the remodeling process can advantageously influence the remodeling process. For example, the remodeling process of one type of remodelable material, extracellular matrix (ECM), is more effective when the material is subject to certain types and ranges of mechanical loading during the remodeling process. See, e.g., M. Chiquet, "Regulation of extracellular matrix gene expression by pressure," Matrix Biol. 18(5), 417-426 (October 1999).

Applying mechanical forces to a remodelable material during the remodeling process can affect processes such as signal transduction, gene expression and contact guidance of cells. Various references describe the influence of mechanical loading on remodelable materials, such as extracellular matrix material (ECM). For example, mediation of numerous physiological and pathological processes by vascular endothelial cells is influenced by mechanical stress, as discussed, for example, in Chien, Shu et al., "Effects of Mechanical Forces on Signal Transduction and Gene Expression in Endothelial Cells," Hypertension 31(2): 162-169 (1998). Expression of bioactive agents can be stimulated by mechanical stress on certain cells involved in remodeling processes, such as fibroblasts, as discussed, for example, by Schild, Christof et al., "Mechanical Stress is Required for High-Level Expression of Connective Tissue Growth Factor," Experimental Cell Research, 274: 83-91 (2002). Furthermore, another study suggests that fibroblasts attached to a remodelable material such as a strained collagen matrix produce increased amounts of ECM glycoproteins like tenascin and collagen XII compared to cells in a relaxed matrix. Chiquet, Matthias, et al., "Regulation of Extracellular Matrix Synthesis by Mechanical Stress," Biochem. Cell. Biol., 74:737-744 (1996). Other studies of remodelable material have found that remodeling processes are sensitive to alterations in mechanical load. See, e.g., Wong, Mary et al., "Cyclic Compression of Articular Cartilage Explants is Associated with Progressive Consolidation and Altered Expression Pattern of Extracellular Matrix Proteins," Matrix Biology, 18: 391-399 (1999); Grodzinsky, Alan J. et al., "Cartilage Tissue Remodeling in Response to Mechanical Forces," Annual Review of Biomedical Engineering, 2: 691-713 (2000). In addition, the alignment of cells with respect to mechanical loads can affect remodeling processes, as studied, for example, by VC Mudera et al., "Molecular responses of human dermal fibroblasts to dual cues: contact guidance and mechanical load," Cell Motil. Cytoskeleton, 45(1):1-9 (June 2000). These references are incorporated herein by reference.

Any suitable remodelable material may be used. Preferably, the remodelable material is an extracellular matrix material (ECM), such as small intestine submucosa (SIS).

A "mechanical load" means any force applied to a material that results in tension within the material. In preferred embodiments, a remodelable material is subject to adequate mechanical load to allow remodeling processes to occur.

To facilitate ingrowth of host or other cells during the remodeling process, either before or after implantation, a variety of biological response modifiers may be incorporated into the remodelable material. Appropriate biological response modifiers may include, for example, cell adhesion molecules, cytokines, including growth factors, and differentiation factors. Mammalian cells, including those cell types useful or necessary for populating the resorbable stent of the present invention, are anchorage-dependent. That is, such cells require a substrate on which to migrate, proliferate and differentiate.

In some embodiments, upon implantation in a body vessel, a remodelable material can be subject to both a mechanical load, for example from the manner of attachment to a frame, as well as a variable shear stress from the fluid flow within the body vessel. For example, Helmlinger, G. et al., disclose a model for laminar flow over vascular endothelial cells in "Calcium responses of endothelial cell monolayers subjected to pulsatile and steady laminar flow differ," Am. J. Physiol. Cell Physiol. 269:C367-C375 (1995).

Shear forces within a body vessel can also influence biological processes involved in remodeling. For example, the role of hemodynamic forces in gene expression in vascular endothelial cells is discussed by Li, Y. S. et al., "The Ras-JNK pathway is involved in shear-induced gene expression," Mol. Cell Biol., 16(11): 5947-54 (1996).

Many other studies of the range of shear forces and the effect of shear forces on the remodeling process are found in the art. Using these references and others, one skilled in the art can select a level of mechanical loading that, when taking into account the range of fluid flow shear forces within a body vessel, will provide optimal mechanical loading conditions for remodeling of the remodelable material.

Figure 6A:
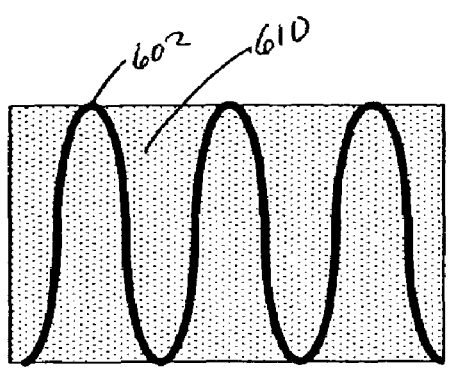
FIGS. 6A-6D show a portion of medical device comprising a support frame and a remodelable material.
Figure 6B:
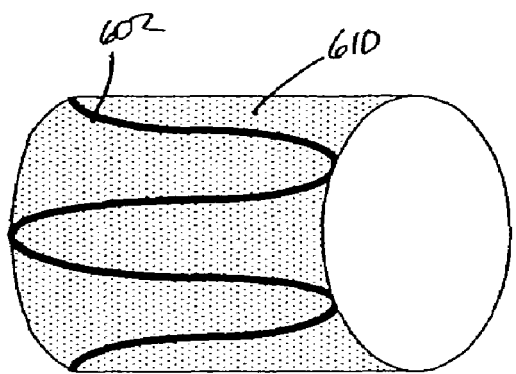

FIG. 6A and FIG. 6B are diagrams of a first medical device comprising a support frame and a remodelable material. The first medical device comprises a sinusoidal frame 602 attached to a sheet of remodelable material 610. The frame 602 maintains a mechanical load on the remodelable material 610 through outward biasing of the bends in the frame. The first medical device is shown in a substantially planar configuration 600 in FIG. 6A, and in a tubular configuration 610 in FIG. 6B. Preferably, the medical device is formed in the tubular configuration, which can be compressed and delivered intraluminally to a body vessel, where it can be expanded upon deployment therein. The first medical device can be initially formed in a tubular configuration 610 without being in the substantially planar configuration 600. For example, a tube of material can be laser cut to form the frame 602 in a tubular configuration 610 and the remodelable material 601 can be attached to the frame 602. Preferably, the frame 602 comprises a self-expanding NiTi alloy material. Alternatively, two ends of the frame 602 or remodelable material segment 610 of the medical device in the flat configuration shown in FIG. 6A can be joined together to form the tubular configuration of FIG. 6B.

Figure 6C:
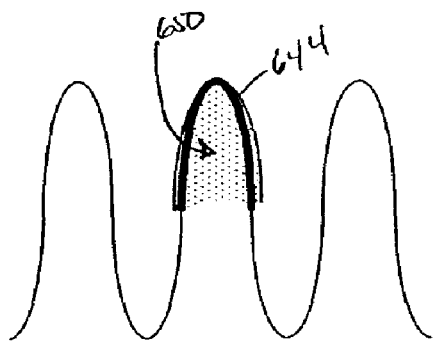
Figure 6D:
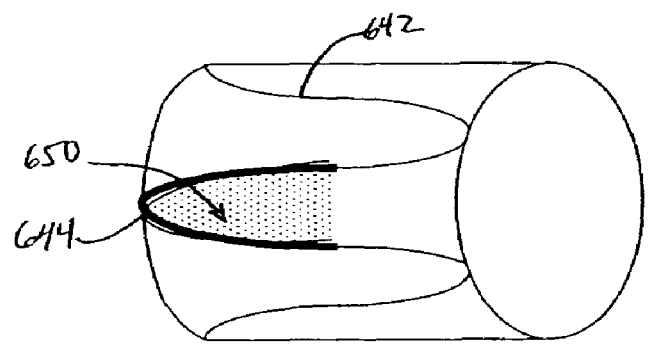

FIG. 6C is a schematic of a portion of a second medical device comprising a support frame and a remodelable material, in a substantially planar configuration. The medical device in a substantially planar configuration comprises a frame 642 that has a first portion 644 that is attached to a remodelable material 650. The first portion 644 maintains a mechanical load on the remodelable material 650 so as to allow the remodeling process to occur upon implantation. As shown in FIG. 6D, the second medical device can also be folded into a tubular configuration for implantation in a body vessel. Alternatively, the second medical device can be initially formed in a tubular configuration without being in the substantially planar configuration. For example, a tube of material can be laser cut to form the frame 642 in a tubular configuration and the remodelable material 650 can be attached to the frame 642. Preferably, the frame 642 comprises a self-expanding NiTi alloy material.

Regulating Fluid Flow

In a third embodiment, the medical device can comprise a frame and a means for regulating fluid through a body vessel. The invention also relates to embodiments comprising a frame and a means for regulating fluid through a body vessel. A medical device can permit fluid within a body vessel to flow through the frame, or permit fluid flow through a lumen defined by the frame. Some embodiments comprise a frame and a first valve member connected to the frame. The valve member can be a flexible leaflet attached to the frame along at least one edge and extending into the lumen of the body vessel. A valve member, can comprise a free edge of a leaflet that is responsive to the flow of fluid through the body vessel. One or more valve members attached to a frame may, in one embodiment, permit fluid to flow through a body vessel in a first direction while substantially preventing fluid flow in the opposite direction. Preferably, the valve member comprises an extracellular matrix material, such as small intestine submucosa (SIS). In one preferred aspect, medical devices comprising a frame and a valve member can be used to regulate fluid flow in a vein, for example to treat venous valve incompetency. For example, one or more medical devices comprising a frame and one or more valve members can be implanted in a vein with incompetent venous valves so as to provide a valve to replace the incompetent valves therein.

A wide variety of materials acceptable for use as the valve members are known in the art, and any suitable material can be utilized. The material chosen need only be able to perform as described herein, and be biocompatible, or able to be made biocompatible. Examples of suitable materials include flexible materials, natural materials, and synthetic materials. Examples of suitable natural materials include collagen and extracellular matrix (ECM) material, such as submucosa. Small intestine submucosa (SIS) is particularly well-suited for use as valve members, such as leaflets. Examples of suitable synthetic materials include polymeric materials, such as polypropylene, polyurethane, expanded polytetrafluoroethylene (ePTFE), polyurethane (PU), polyalkylsiloxane compounds (including polydimethylsiloxane), polyethylene terphthalate (PET), silicone, latex, polyethylene, polypropylene, polycarbonate, nylon, polytetrafluoroethylene, polyimide, polyester, and mixture or combinations thereof, or other suitable materials. In one aspect, the valve member is formed from a polyurethane with about 1-5% polydimethylsiloxane additive incorporated therein to provide a surface energy of about 20-22 dyne/cm. A polyurethane valve member can optionally be made porous by the addition of watersoluble salts to the dissolved polyurethane during the formation of the valve member, followed by subsequent removal of the salts to leave pores in the polyurethane valve member.

The valve members can be attached to the frame with any suitable attachment mechanism, such as sutures, adhesives, bonding, and the like. The attachment mechanism chosen will depend on the nature of the frame and valve members. Sutures provide an acceptable attachment mechanism when SIS or other ECM materials are used as the valve members with a metal or plastic frame. The device can include any suitable number of valve members. The valve members need only be able to provide the functionality described herein. The specific number chosen will depend on several factors, including the type and configuration of the frame.

In some embodiments, the frame provides one or more structural features that protect a valve member. For example, the frame can include a portion positioned between a portion of a leaflet and the interior wall of a body vessel upon implantation. Another example of a protecting feature in a frame includes arms or members of the frame extending between portions of a leaflet and the inner wall of a body vessel. As another example, a narrowed portion of an inner diameter of a frame around a leaflet can protect a portion of the leaflet from adhering to the inner wall of a body vessel upon implantation of a medical device therein. In one embodiment, the leaflet can comprise a remodelable material and the protecting structural feature of the frame can be bioabsorbed gradually in a time period sufficient for remodeling of at least a portion of the leaflet. Bioabsorption of the protecting feature of the frame can also gradually increase the compliance of the frame. In another embodiment, the protecting feature of the frame can fracture in a controlled manner, for instance by microfractures along a portion of the frame, after a suitable period of implantation (for example after about 30 days post implantation). Frames that comprise materials that increase frame compliance upon implantation by other means such as the absorption of fluid, responsive to changes in pH or body temperature, or various biochemical processes can also be used, for example as a structural feature to protect a leaflet or portion thereof from undesirable contact with the inner wall of a body vessel.

FIG. 7A shows a medical device in a substantially planar configuration 700, according to one embodiment, comprising a frame 710 and two valve members. The frame 710 comprises two "zig-zag" frame members joined to form a linear chain of diamond-shaped cells. The two valve members are a first leaflet 720 and a second leaflet 724. Each leaflet has three sides and is attached to the frame 710 along two sides of the leaflet. Leaflets may be made of any suitable material. In one embodiment, a leaflet comprises a remodelable material such as an extracellular matrix material (for example, SIS). In another embodiment, a leaflet comprises a suitable synthetic material. Non-limiting examples of suitable synthetic materials include polymeric materials, such as polypropylene, polyurethane, and expanded polytetrafluoroethylene (ePTFE), polyurethane (PU), polyethylene terphthalate (PET), silicone, latex, polyethylene, polypropylene, polycarbonate, nylon, polytetrafluoroethylene, polyimide, polyester, and mixture thereof, or other suitable materials.

The first leaflet 720 is attached to the frame along a first edge 722 and along a second edge 723 by suturing the leaflet around the frame. The remaining third edge 721 is a free edge that is flexible enough to move in response to fluid flowing past the leaflet. Similarly, the second leaflet 724 is attached to the frame along a first edge 726 and along a second edge 727 by suturing the leaflet around the frame. The remaining third edge 725 is a free edge that is flexible enough to move in response to fluid flowing past the leaflet.

In FIG. 7B, and corresponding end views of FIGS. 7C-7D, the frame 710 can be formed in a tubular configuration 730. The tubular configuration is expandable between a low-profile compressed configuration having a circular cross section and the expanded configuration with an elliptical cross section 750. The tubular configuration 730 is deployed with its longitudinal axis 760 substantially parallel to that of the lumen of a body vessel. The tubular configuration 730 includes a lumen 732 that allows fluid flow in a first direction 740, while substantially reducing or preventing fluid flow in the opposite direction 742, by action of the leaflets in response to fluid flow within the body vessel. In the tubular configuration, the first leaflet 720 and the second leaflet 724 are disposed opposite each other, so as to form a coaptation region 762 where the two leaflets can cooperate to regulate fluid flow through a lumen 732 parallel to a body vessel. The coaptation region 762 is a length along which the valve members contact each other when the valve members are in a closed configuration. In this case, the free edge of first leaflet 720 and the free edge of the second leaflet 724 can contact each other to regulate fluid flow through the frame. More specifically, the free edges of one or more leaflets can be pushed to an open configuration 754 (FIG. 7C) in response to fluid flow in a first direction 740 through a body vessel 732. The free edges of one or more leaflets can form a closed configuration (FIG. 7D) 752 to substantially prevent retrograde fluid flow in a second direction 742, opposite the first direction 740. One or more valve members can define a valve orifice 755 through which fluid in the body vessel can pass. In the embodiment illustrated in FIG. 7B, and end views of FIGS. 7C-7D, the free edges of each leaflet can open to form a valve orifice 755 through which fluid can flow in a first direction 740. In some embodiments, the frame 710 can comprise one or more barbs that can secure the tubular configuration 730 within the body vessel 732. In some embodiments, a first and a second valve member each attached to a frame and each comprising a leaflet free edge moveable in response to fluid flow, can cooperably define a valve orifice through which fluid can flow.

The overall configuration, cross-sectional area, and length of the tubular configuration will depend on several factors, including the size and configuration of the device, the size and configuration of the vessel in which the device will be implanted, the extent of contact between the device and the walls of the vessel, and the amount of retrograde flow through the vessel that is desired.

Although the medical devices in FIGS. 7A-7D are shown with two valve members, other embodiments provide medical devices comprising 1, 2, 3, 4, 5, 6, 7, 8 or more valve members. The valve members can be arranged in any suitable configuration with respect to one another and the frame. In one preferred embodiment, a medical device can comprise a frame and three valve members that are leaflets comprising free edges. In another preferred embodiment, a medical device can comprise one leaflet having a free edge that can sealably engage the interior of a vessel wall. Other suitable configurations of valve members are provided by further embodiments, including differently shaped valve members, and different points of attachment by valve members to the frame.

In devices including multiple openings that permit a controlled amount of fluid flow in the second, opposite direction to flow through the vessel in which the device is implanted, the total open area of all openings can be optimized as described above, but it is not necessary that the individual openings have equivalent total open areas.

The invention also provides methods of making medical devices for implantation in a body vessel. In one embodiment, the method comprises the step of attaching a first valve member to a frame. The valve member can be responsive to the flow of fluid through the frame, and adapted to permit fluid flow through said vessel in a first direction or substantially prevent fluid flow through said vessel in a second, opposite direction. The frame can have a longitudinal axis, a first radial compressibility along a first radial direction that is less than a second radial compressibility along a second radial direction.

Delivery of Medical Devices

The medical devices can be configured for delivery to a body vessel. For example, a medical device can be compressed to a delivery configuration within a retaining sheath that is part of a delivery system, such as a catheter-based system. Upon delivery, the medical device can be expanded, for example, by removing a self-expanding frame, or portion thereof, from the sheath or by inflating a balloon from inside the medical device. The delivery configuration can be maintained prior to deployment of the medical device by any suitable means, including a sheath, a suture, a tube or other restraining material around all or part of the compressed medical device, or other methods.

Medical devices can be deployed in a body lumen by means appropriate to their design. The medical devices of the present invention can be adapted for deployment using conventional methods known in the art and employing percutaneous transluminal catheter devices. The medical devices are designed for deployment by any of a variety of in situ expansion means.

The medical device may be mounted onto a catheter that holds the medical device as it is delivered through the body lumen and then releases the medical device and allows it to self-expand into contact with the body lumen. This deployment is effected after the medical device has been introduced percutaneously, transported transluminally and positioned at a desired location by means of the catheter. The restraining means may comprise a removable sheath. The self-expanding medical device according to the invention may be deployed according to well-known deployment techniques for self-expanding medical devices. The medical device is positioned at the distal end of a catheter with a lubricous sleeve placed over the medical device to hold the medical device in a contracted state with a relatively small diameter. The medical device may then be implanted at the point of treatment by advancing the catheter over a guidewire to the location of the lesion and then withdrawing the sleeve from over the medical device. The medical device will automatically expand and exert pressure on the wall of the blood vessel at the site of the lesion. The catheter, sleeve, and guidewire may then be removed from the patient.

For example, the tubular body of the medical device is first positioned to surround a portion of an inflatable balloon catheter. The medical device, with the balloon catheter inside is configured at a first, collapsed diameter. The medical device and the inflatable balloon are percutaneously introduced into a body lumen, following a previously positioned guidewire in an over-the-wire angioplasty catheter system, and tracked by a fluoroscope, until the balloon portion and associated medical device are positioned within the body passageway at the point where the medical device is to be placed. Thereafter, the balloon is inflated and the medical device is expanded by the balloon portion from the collapsed diameter to a second expanded diameter. After the medical device has been expanded to the desired final expanded diameter, the balloon is deflated and the catheter is withdrawn, leaving the medical device in place. The medical device may be covered by a removable sheath during delivery to protect both the medical device and the vessels.

While the terms "contracted" and "compressed" have been used to describe the medical device as having the small diameter necessary for delivery to an implantation site, it will be appreciated that the terms, especially as applied to pressure-expandable medical devices, should not be used to imply that the tube is under external pressure to provide the tube with a small diameter; i.e., a "contracted" or "compressed" pressure-expandable medical device may be formed and naturally reside in the "contracted" or "compressed" state until internally pressurized to expand. Therefore, "contracted" and "compressed" are intended only to imply that the medical device is in a state of having a small diameter relative to an expanded state. It will therefore be appreciated by those skilled in the art that yet other modifications could be made to the provided invention without deviating from its spirit and scope as so claimed.

In some embodiments, a bioabsorbable suture or sheath can be used to maintain a medical device in a compressed configuration both prior to and after deployment. As the bioabsorbable sheath or suture is degraded by the body after deployment, the medical device can expand within the body vessel. In some embodiments, a portion of the medical device can be restrained with a bioabsorbable material and another portion allowed to expand immediately upon implantation. For example, a self-expanding frame can be partially restrained by a bioabsorbable material upon deployment and later expand as the bioabsorbable material is absorbed.

Methods for delivering a medical device as described herein to any suitable body vessel are also provided, such as a vein, artery, biliary duct, ureteral vessel, body passage or portion of the alimentary canal.

Methods of Treatment

Still other embodiments provide methods of treating a subject, which can be animal or human, comprising the step of providing one or more frames as described herein. Other methods further comprise the step of providing one or more frames attached to one or more valve members, as described herein. In some embodiments, methods of treatment may also provide the step of delivering a medical device to a point of treatment in a body vessel, or deploying a medical device at the point of treatment, wherein the medical devices are as described herein.

The invention also provides methods of treating a patient. In one embodiment the method comprises a step of delivering a medical device as described herein to a point of treatment in a body vessel, and deploying the medical device at the point of treatment. The delivering step can comprise delivery by surgical or by percutaneous delivery techniques known to those skilled in the art.

Methods for treating certain conditions are also provided, such as venous valve insufficiency, varicose veins, esophageal reflux, restenosis or atherosclerosis. In some embodiments, the invention relates to methods of treating venous valve-related conditions.

A "venous valve-related condition" is any condition presenting symptoms that can be diagnostically associated with improper function of one or more venous valves. In mammalian veins, venous valves are positioned along the length of the vessel in the form of leaflets disposed annularly along the inside wall of the vein which open to permit blood flow toward the heart and close to prevent back flow. These venous valves open to permit the flow of fluid in the desired direction, and close upon a change in pressure, such as a transition from systole to diastole. When blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to restrict or prevent blood flow in the opposite, i.e. retrograde, direction after the pressure is relieved. The leaflets, when functioning properly, extend radially inwardly toward one another such that the tips contact each other to block backflow of blood. Two examples of venous valve-related conditions are chronic venous insufficiency and varicose veins.

In the condition of venous valve insufficiency, the valve leaflets do not function properly. For example, the vein can be too large in relation to the leaflets so that the leaflets cannot come into adequate contact to prevent backflow (primary venous valve insufficiency), or as a result of clotting within the vein that thickens the leaflets (secondary venous valve insufficiency). Incompetent venous valves can result in symptoms such as swelling and varicose veins, causing great discomfort and pain to the patient. If left untreated, venous valve insufficiency can result in excessive retrograde venous blood flow through incompetent venous valves, which can cause venous stasis ulcers of the skin and subcutaneous tissue. Venous valve insufficiency can occur, for example, in the superficial venous system, such as the saphenous veins in the leg, or in the deep venous system, such as the femoral and popliteal veins extending along the back of the knee to the groin.

The varicose vein condition consists of dilatation and tortuosity of the superficial veins of the lower limb and resulting cosmetic impairment, pain and ulceration. Primary varicose veins are the result of primary incompetence of the venous valves of the superficial venous system. Secondary varicose veins occur as the result of deep venous hypertension which has damaged the valves of the perforating veins, as well as the deep venous valves. The initial defect in primary varicose veins often involves localized incompetence of a venous valve thus allowing reflux of blood from the deep venous system to the superficial venous system. This incompetence is traditionally thought to arise at the saphenofemoral junction but may also start at the perforators. Thus, gross saphenofemoral valvular dysfunction may be present in even mild varicose veins with competent distal veins. Even in the presence of incompetent perforation, occlusion of the saphenofemoral junction usually normalizes venous pressure.

The initial defect in secondary varicose veins is often incompetence of a venous valve secondary to hypertension in the deep venous system. Since this increased pressure is manifested in the deep and perforating veins, correction of one site of incompetence could clearly be insufficient as other sites of incompetence will be prone to develop. However, repair of the deep vein valves would correct the deep venous hypertension and could potentially correct the secondary valve failure. Apart from the initial defect, the pathophysiology is similar to that of varicose veins.

While many preferred embodiments discussed herein discuss implantation of a medical device in a vein, other embodiments provide for implantation within other body vessels. In another matter of terminology there are many types of body canals, blood vessels, ducts, tubes and other body passages, and the term "vessel" is meant to include all such passages.

The invention includes other embodiments within the scope of the claims, and variations of all embodiments, and is limited only by the claims made by the Applicants.

We claim:

1. A medical device for implantation in a body vessel, the medical device comprising:
 a tubular, implantable frame defining a lumen about a longitudinal axis and having a first frame member including a plurality of struts and bends interconnecting the struts, the first frame member comprising a non-bioabsorbable material, and a second frame member including a plurality of struts and bends interconnecting the struts, the second frame member configured to increase in compliance after implantation of said medical device, the second frame member attached to the first frame member at least at two attachment points and disposed radially outward such that the second frame is to contact said body vessel, the implantable frame being radially movable between an expanded configuration and a compressed configuration, the implantable frame having a first compliance in a first radial direction at implantation and a second compliance in the first radial direction after passage of a predetermined period of time after implantation; and a valve leaflet comprising a remodelable material, the valve leaflet being attached to the frame between the two attachment points, wherein at the two attachment points a portion of the valve leaflet is interposed between the first and second frame members to protect the valve leaflet from contacting the body vessel, wherein the implantable frame having the first compliance maintains a mechanical load on the valve leaflet to promote remodeling for the predetermined period of time.

2. The medical device of claim 1, wherein the valve leaflet is positioned within the lumen of the frame.

3. The medical device of claim 1, wherein the valve leaflet comprises a first edge attached to the frame and a second edge attached to the frame, wherein the valve leaflet has a first tension between the first and second edge when the implantable frame has the first compliance.

4. The medical device of claim 1, wherein the valve leaflet is a first valve leaflet, the medical device further comprising a second valve leaflet comprising a remodelable material, the second valve leaflet comprising a first edge attached to the frame and a second edge attached to the frame, wherein the second valve leaflet has a first tension between the first and second edge of the second valve leaflet when the implantable frame has the first compliance, and wherein the first valve leaflet and the second valve leaflet are disposed opposite each other to form a coaptation region where the first and second valve leaflets can cooperate to regulate fluid flow through the lumen.

5. The medical device of claim 1, wherein the second frame member, comprises a bioabsorbable material.

6. The medical device of claim 5, wherein the bioabsorbable material is selected from the group consisting of: poly(L-lactic acid), polylactic acid, poly(glycolic acid), poly(epsilon-caprolactone), poly(dimethyl glycolic acid), poly(hydroxy butyrate), poly(p-dioxanone), polydioxanone, PEO/PLA, poly(lactide-co-glycolide), poly(hydroxybutyrate-co-valerate), poly(glycolic acid-co-trimethylene carbonate), poly(epsilon-caprolactone-co-p-dioxanone), poly-L-glutamic acid or poly-L-lysine, polylactic acid, polylactide, polyglycolic acid, polyglycolide, polyhydroxyvalerate, cellulose, chitin, dextran, fibrin, casein, fibrinogen, starch, collagen, hyaluronic acid, hydroxyethyl starch, gelatin.

7. The medical device of claim 1, wherein the non-bioabsorbable material is selected from the group consisting of: a shape memory material, a superelastic material, a stainless steel, a cobalt-chromium alloy, a NiTi alloy, MP35N, gold, tantalum, platinum, platinum iridium, and a carbon fiber.

8. The medical device of claim 1, wherein the attachment of the first and second frame members form an array of diamond-shaped cells.

9. The medical device of claim 1, wherein the valve leaflet has a first edge and a second edge attached along the struts of the first frame member.

10. The medical device of claim 9, wherein the valve leaflet has a first tension between the first and second edge when the implantable frame has the first compliance.

11. The medical device of claim 1, wherein the valve leaflet has three edges, wherein two of the three edges are attached along the struts of the first frame member and the other edge of the three edges is unattached to the frame and disposed across the lumen of the frame.

12. The medical device of claim 1, wherein the plurality of bends of the second frame member includes a bend portion comprising a bioabsorbable material, where upon bioabsorption of the bend portion the frame has the second compliance.

13. The medical device of claim 1, wherein the plurality of bends of the second frame member includes a bend portion configured to fracture in a controlled fashion along a fracture line, where upon fracturing the bend portion the frame has the second compliance.

14. The medical device of claim 1, where the remodelable material comprises an extracellular matrix material.

15. The medical device of claim 1, wherein the remodelable material comprises small intestine submucosa.

16. The medical device of claim 1, further comprising a means for orienting the frame within a body vessel.

17. The medical device of claim 1, wherein the tubular frame in the expanded configuration has an elliptical cross-section and in the compressed configuration has a circular cross-section.

18. The medical device of claim 1, wherein the tubular frame comprises one or more barbs to secure said frame within said body vessel.

19. A medical device for implantation in a body vessel, the medical device comprising:

a tubular, implantable frame defining a lumen about a longitudinal axis and having a first frame member including a plurality of struts and bends interconnecting the struts, the first frame member comprising a non-bioabsorbable material, and a second frame member including a plurality of struts and bends interconnecting the struts, the second frame member comprising a bioabsorbable material configured to degrade during passage of a predetermined period of time after implantation, the second frame member attached to the first frame member at least at two attachment points and disposed radially outward such that the second frame is to contact said body vessel, the implantable frame being radially movable between an expanded configuration and a compressed configuration, the implantable frame having a first compliance in a first radial direction at implantation and a second compliance less than the first compliance in the first radial direction after passage of the predetermined period of time; and a valve leaflet comprising a remodelable material, the valve leaflet being attached along the struts of the first frame member between the two attachment points and disposed across the frame lumen, wherein at the two attachment points a portion of the valve leaflet is interposed between the first and second frame members to protect the valve leaflet from contacting the body vessel, wherein the implantable frame having the first compliance maintains a mechanical load on the valve leaflet to promote remodeling during the predetermined period of time.

20. A medical device for implantation in a body vessel, the medical device comprising:

a tubular, implantable frame defining a lumen about a longitudinal axis and having a first frame member including a plurality of struts and bends interconnecting the struts, the first frame member comprising a non-bioabsorbable material, and a second frame member including a plurality of struts and bends interconnecting the struts, the second frame member comprising a bioabsorbable material configured to degrade during passage of a predetermined time after implantation, the second frame member attached to the first frame member at least at two attachment points and disposed radially outward such that the second frame is to contact said body vessel, the implantable frame being radially movable between an expanded configuration and a compressed configuration, the implantable frame having a first compliance in a first radial direction at implantation and a second compliance less than the first compliance in the first radial direction after passage of the predetermined period; and a first valve leaflet and a second valve leaflet each comprising a remodelable material, the first and second valve leaflets being attached along the struts of the first frame member between two attachment points and disposed across the frame lumen, the first and second valve leaflets being disposed opposite each other to form a coaptation region where the leaflets cooperate to regulate fluid flow through the frame lumen, wherein at the two attachment points a portion of the first and second valve leaflets is interposed between the first and second frame members to protect the valve leaflets from contacting the body vessel, wherein the implantable frame having the first compliance maintains a mechanical load on the valve leaflets to promote remodeling during the predetermined period of time.

* * * * *

UNITED STATES PATENT AND TRADEMARK OFFICE
CERTIFICATE OF CORRECTION

PATENT NO. : 7,582,110 B2
APPLICATION NO. : 11/103137
DATED : September 1, 2009
INVENTOR(S) : Case et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 546 days.

Signed and Sealed this

Fourteenth Day of September, 2010

David J. Kappos
*Director of the United States Patent and Trademark Office*